United States Patent
Crouzet et al.

(10) Patent No.: US 9,511,136 B2
(45) Date of Patent: Dec. 6, 2016

(54) IMMUNOGENIC COMPOUNDS COMPRISING HIV GP41 PEPTIDE COUPLED TO CRM197 CARRIER PROTEIN

(71) Applicant: INNAVIRVAX, Evry (FR)

(72) Inventors: Joël Crouzet, Sceaux (FR); Raphaël Ho Tsong Fang, Paris (FR); Dominique Desfontaines, Paris (FR)

(73) Assignee: INNAVIRVAX, Evry (FR)

( * ) Notice: Subject to any disclaimer, the term of this patent is extended or adjusted under 35 U.S.C. 154(b) by 0 days.

(21) Appl. No.: 14/404,254

(22) PCT Filed: May 30, 2013

(86) PCT No.: PCT/IB2013/054482
§ 371 (c)(1),
(2) Date: Nov. 26, 2014

(87) PCT Pub. No.: WO2013/179262
PCT Pub. Date: Dec. 5, 2013

(65) Prior Publication Data
US 2015/0147348 A1    May 28, 2015

(30) Foreign Application Priority Data

May 31, 2012 (EP) .................................... 12305602

(51) Int. Cl.

| A61K 39/21 | (2006.01) |
|---|---|
| A61K 39/12 | (2006.01) |
| A61K 47/48 | (2006.01) |
| A61K 39/00 | (2006.01) |
| C07K 16/10 | (2006.01) |
| C12N 7/00 | (2006.01) |

(52) U.S. Cl.
CPC ............... *A61K 39/21* (2013.01); *A61K 39/12* (2013.01); *A61K 47/48261* (2013.01); *C07K 16/1063* (2013.01); *C12N 7/00* (2013.01); *A61K 2039/53* (2013.01); *A61K 2039/55505* (2013.01); *A61K 2039/6037* (2013.01); *A61K 2039/6081* (2013.01); *A61K 2039/627* (2013.01); *C12N 2740/16134* (2013.01)

(58) Field of Classification Search
None
See application file for complete search history.

(56) References Cited

FOREIGN PATENT DOCUMENTS

WO     2010022740 A2    3/2010
WO     WO 2010/027740  *  4/2010

OTHER PUBLICATIONS

Zhang et al., Molecular Medicine reports, 2011, 4:857-863.*
Matthews et al., 1987, AIDS Research and Human Retroviruses, 3(1):197-206.*
Burton and Moore, Nature Medicine, 1998, 4(5):495-498.*
Desrosiers, Nature Medicine, 2004, 10(3):221-223.*
Zhang et al., "A novel combined conjugate vaccine: Enhanced immunogenicity of bFGF with CRM 197 as a carrier protein," Molecular Medicine Reports, vol. 4, pp. 857-863 (2011).
Viellard et al., "A vaccine strategy against AIDS: An HIV gp41 peptide immunization prevents NKp44L expression and CD4+ T cell depletion in SHIV-infected macaques," PNAS, vol. 105, No. 6, pp. 2100-2104 (Feb. 12, 2008).

* cited by examiner

*Primary Examiner* — Nicole Kinsey White
(74) *Attorney, Agent, or Firm* — Law Office of Scott Lee and Salvatore Arrigo, LLP

(57) ABSTRACT

The present invention relates to the field of vaccines directed against viruses of the HIV family. More particularly, it relates to an immunogenic compound comprising a peptide of the following formula (I) NH2-[Nt]y-P-W-N-X-S-X2-S-N-X3-X4-X-X6-X7-I-W-[Ct]z-COOH (I) which is covalently linked to a carrier protein consisting of a CRM197 protein. It also concerns a composition containing this immunogenic compound and the uses of these immunogenic compounds and compositions for preventing and/or treating a condition caused by the infection of an individual with a HIV virus.

20 Claims, 5 Drawing Sheets

IMMUNOGENIC COMPOUNDS COMPRISING HIV GP41 PEPTIDE COUPLED TO CRM197 CARRIER PROTEIN

FIELD OF THE INVENTION

The present invention relates to the field of vaccines directed against viruses of the HIV family.

BACKGROUND

About 90% of the human HIV infections are caused by a HIV-1 virus. Human immunodeficiency virus type 1 (HIV-1) is characterized by a striking genetic variability caused by accumulation of mutations, arising during viral replication, and also caused by the recombination events. Long term failure of chemotherapeutic methods of HIV treatment is notably explained by the high mutagenic activity of HIV-1 viral strains. It was shown earlier that resistant viral variants quickly have been arisen in patients after different courses of antiretroviral therapy and even after multidrug therapy (HAART). These resistant viruses bear specific alterations in their proteins conformation and structure. Usually such mutations responsible for HIV-1 escape from current treatments are maintained through the successive virus generations and accumulate, as a result of selection under the treatment conditions.

Treatment with anti-HIV-1 medicines does not totally block replication of the virus, which allows a selection and accumulation of pre-existing resistance mutations, as well as of newly occurring mutations, thus bringing new opportunities for the virus to go on spreading. The existing antiretroviral medicines (NRTI, NNRTI, protease inhibitors, fusion inhibitors and mixtures thereof, like HAART) can only slow down the HIV-1 replication for a more or less prolonged period of time, until the arising and propagation of resistant viral strains. The wide spreading of HIV-1 resistant variants raises serious concerns and requires the availability for further anti-HIV-1 therapeutic tools.

Furthermore, despite clear clinical benefits of HAART, drawbacks persist: many side effects (lipodystrophy, lactic acidosis, insulin resistance, chronic kidney disease, hyperlipidemia . . . ), life-time treatment, high compliance required, viral resistances, persistence of pathogenic effects of HIV infection, as cognitive and motor deficits, and immune activation. Moreover, with the extension of life-expectancy, patients must face emergence of side effects, drug resistances, metabolic disorders and cancers associated with HIV-1 infection.

In addition, 20% to 30% of the treated patients experience an immunological failure sometimes despite a viral suppression. That is to say that their CD4+ T cell counts decrease despite the inhibition of viral replication. This shows that pathogenic events of HIV-1 infection on CD4+ T cell still exist despite the inhibition of viral replication. So, a safe and affordable therapeutic approach that could be complementary to antiretroviral treatments, protecting the CD4+ T cells is needed and represents an unmet medical need.

Various anti-HIV therapeutic strategies, other than those making use of chemical anti-retroviral substances, have been considered, which include (i) the use of anti-HIV antibodies, (ii) HIV particles disruption-based vaccines, (iii) HIV peptides-based vaccines and (iv) DNA plasmid or viral vector-based vaccines, each having their specific drawbacks.

Since HIV was identified as the cause of AIDS in 1983, multiple candidates for a vaccine to prevent HIV infection and AIDS have been tested in human trials with very limited success. The international AIDS vaccine initiative, IAVI, maintains a database of these vaccines and trials. Nearly all of these trials have been very early (phase I) tests of vaccine safety and preliminary immune response. Only one vaccine (two formulations of the same basic gpI20 vaccine) has been tested in large-scale Phase III studies. The VaxGen gpI20 subtype B protein was found ineffective in a phase III trial that was completed in 2003 in USA, Canada and Netherlands. Later in 2003, a second trial of AIDSVAX was completed in Thailand. Both trials found the candidates to be ineffective. It has previously been difficult to prepare protein vaccines against HIV which may be due to the high diversity in the envelope protein, the differences between the envelope of the laboratory adapted strain used and the clinical isolates, the monomeric nature of the gpI20 in the vaccine and the trimeric organisation in the virus, and in particular because only antibodies and not cellular immunity are induced. A combination of AIDSVAX protein (from VAX-Gene) with genes delivered in canary pox (ALVAC from Aventis Pasteur) is also in phase III for further information) and a fourth large scale trial is expected to begin testing Merck's adenovirus-based candidate. Cytotoxic T-lymphocytes (CTL) are considered a critical component of immune control of virus including HIV-I and relevant CTL immunogens are considered for therapeutic vaccines.

As the HIV pandemic continues to infect millions of people each year, the need for an effective vaccine increases. The development of anti-HIV vaccines has been deeply impaired, due to the difficulty in developing an immunogenic product capable of eliciting broadly neutralizing anti-HIV antibodies.

Induction of broadly neutralizing antibodies (NtAb) against primary isolates of human immunodeficiency virus (HIV) remains a major and unmet goal for AIDS vaccine research. Early attempts using envelope-based vaccines have elicited antibodies that are effective only against laboratory-adapted isolates. In these instances, protection has been correlated with high titer NtAb directed to the V3 hypervariable region of gp120. However, neutralizing activities generated are largely isolate-specific and are minimally effective against most primary isolates of HIV-1. The failure of subunit gp120 vaccines to protect against HIV-1 acquisition in Phase III clinical trials underscores the difficulty of the task.

Nevertheless, NtAb can often be found in HIV infected individuals. Responses generated early in infection are usually narrow in specificity, neutralizing the transmitted viruses in the host, but not the contemporaneous ones. Such responses broaden during the course of infection in some long-term survivors who are able to control their infection in the absence of antiviral treatment. However, the nature of the cross-neutralizing antibody response and the mechanisms leading to its genesis are not understood.

Naturally, NtAbs against Env are generated within weeks after infection, but this early response is only efficient against a specific viral subtype; however, bNtAbs (cross-reactive neutralizing Abs) can develop during the course of HIV. Recently several major studies have shown that approximately 25% of HIV-infected subjects (infected for at least 1 yr) have bNtAb response, and 1% of "Elite neutralizers' with very robust activity against a great majority of clades. Importantly, these results demonstrate the ability of the immune system of infected persons to in vivo generate NtAbs against HIV-1, during the course of the disease. They also suggest that broadly reactive NtAb activities seem to develop over time and are fostered by chronic antigen exposure, in absence of knowledge about the titer of bNtAbs that would be protective.

Persistent viral replication, in low noise, leads to a continuous evolution of Env to evade NtAbs. Such antigenic evolution may focus new vaccine strategy on the more conserved region of the Env protein, and suggest that vaccine immunogens could be designed to mimic key highly conserved epitopes.

One of the major obstacles to the design of efficient anti-HIV vaccines has been that the target of bNtAbs is the viral envelope protein (Env), which is highly variable, whereas the conserved elements seem to be poorly immunogenic. This means that kinetic and special constraints impede bNtAbs from accessing potentially vulnerable sites during receptor binding and fusion processes. Actually few amount of NtAbs have been described. For example, the first bNtAb identified was b12, which occludes the CD4 binding site on gp120 and prevents CD4 attachment of the virus on CD4+ T lymphocytes. The gp41 subunit is far more conserved than is gp120 involving conformational rearrangements is common to all stains. Very little bNtAb activities are elicited against conserved structural elements of the gp41 that are shielded, difficult to access or transient; those bNtAbs, including 2F5 and 4E10, targets the membrane-proximal ectodomain region (MPER) of gp41. However, despite many years of research, NtAb immunogens able to elicit these bNtAbs are still unknown as the epitopes are conformational.

Despite numerous difficulties encountered in designing safe and efficient preventive or therapeutic vaccine strategies against infection with an HIV virus, great progress have been made in the conception of promising anti-HIV vaccine compositions. Illustratively, not less than 576 clinical studies of anti-HIV vaccines were being conducted at the beginning of the year 2012 in the United States, Canada and Australia. It is worth mentioning that 27 of these clinical studies have a completed Phase IV stage. These advances show that, with time, anti-HIV vaccines represent increasingly tangible and credible medical tools for preventing and/or treating individuals who are at risk or who are already subjects to infection with an HIV virus. All these vaccines in development aim at reducing the viral replication of the virus.

One of the promising preventive, as well as therapeutic anti-HIV vaccine strategies disclosed in the art relates to the raising of antibodies against a highly conserved motif of the HIV gp41 envelope protein, which was named "3S". It has been shown in the art that an immunogenic composition consisting of the 3S peptide coupled to the KLH carrier protein (named KLH-3S) in combination with the Incomplete Freund's Adjuvant (IFA) was able to induce anti-3S antibodies in macaques. It has also been shown that the anti-3S antibodies had a protective effect against the CD4+ T cell decline in the immunized macaques. These results opened the way for additional strategies of immune intervention aimed at controlling HIV disease development (Vieillard et al., 2008, PNAS, Vol. 105 (6): 2100-2104).

This strategy is the first to target a viral determinant of HIV-1 pathogenicity and not the viral replication.

There is still a need in the art for therapeutic tools aimed at preventing or treating an infection caused by an HIV-1 virus.

SUMMARY OF THE INVENTION

The present invention relates to an immunogenic compound comprising a peptide of the following formula (I)

$$NH_2\text{-}[Nt]_y\text{-}P\text{-}W\text{-}N\text{-}X_1\text{-}S\text{-}X_2\text{-}S\text{-}N\text{-}X_3\text{-}X_4\text{-}X_5\text{-}X_6\text{-}X_7\text{-}I\text{-}W\text{-}[Ct]_z\text{-}COOH \quad (I),$$

wherein:
y is an integer meaning 0 or 1,
z is an integer meaning 0 or 1,
Nt consists of a peptide having from 1 to 100 amino acids in length,
Ct consists of a peptide having from 1 to 100 amino acids in length,
$X_1$ is an amino acid selected from the group consisting of A (Alanine), T (threonine), S (Serine) and N (Asparagine),
$X_2$ is an amino acid selected from the group consisting of W (Tryptophane) and A (Alanine),
$X_3$ is an amino acid selected from the group consisting of K (Lysine) and R (Arginine,
$X_4$ is an amino acid selected from the group consisting of S (Serine) and T (Threonine),
$X_5$ is an amino acid selected from the group consisting of L (Leucine), Y (Tyrosine) and Q (Glutamine),
$X_6$ is an amino acid selected from the group consisting of D (Aspartic acid), N (Asparagine), E (Glutamic acid), S (Serine), G (Glycine) and K (Lysine),
$X_7$ is an amino acid selected from the group consisting of D (Aspartic acid), Q (Glutamine), L (Leucine), A (Alanine), K (Lysine) and E (Glutamic acid), which peptide of formula (I) is covalently linked to a carrier protein consisting of a CRM 197 protein.

In some embodiments, the immunogenic compound comprises the peptide of SEQ ID No 2 [$NH_2$-PWNASWSNK-SLDDIW-COOH] which is covalently bound to a carrier protein consisting of the CRM 197 protein.

Notably, the present invention concerns an immunogenic compound comprising a peptide of the following formula (V)

$$NH_2\text{-}(A1)_m\text{-SEQ IDNo2-}(A2)_n\text{-COOH} \quad (V),$$

wherein:
m is an integer meaning 0 or 1,
n is an integer meaning 0 or 1,
A1 is an amino acid residue, and
A2 is an amino acid residue, which peptide of formula (I) is covalently linked to a carrier protein consisting of a CRM 197 protein.

In some embodiments of an immunogenic compound according to the invention, the peptide of formula (I) comprises, or consists of, a peptide of SEQ ID No 5.

In some other embodiments of an immunogenic compound according to the invention, the peptide of formula (I) comprises, or consists of, a peptide of SEQ ID No 6.

In some embodiments, the said immunogenic compound is covalently bound to the said carrier protein by its N-terminal end amino acid residue, either directly or through a linker moiety.

Thus, in some embodiments, the said immunogenic compound is covalently bound to the said carrier protein through a linker moiety, preferably a linker moiety comprising two reactive succinimidyl groups.

This invention also pertains to a composition comprising an immunogenic compound as defined above in combination with one or more immunoadjuvant substances.

Preferably, the said one or more immunoadjuvant substances comprise, or consists of, aluminium hydroxide (Al(OH)$_3$).

The present invention also deals with a vaccine composition comprising an immunogenic compound or a composition as defined above, in combination with one or more pharmaceutically acceptable carrier.

This invention also concerns an immunogenic compound or a composition as defined above, for use a medicament, or alternatively for use for preventing and/or treating a condition caused by the infection of an individual with a HIV virus.

It also relates to the use of an immunogenic compound or of a composition as defined above, for preparing a vaccine composition for preventing and/or treating a condition caused by the infection of an individual with a HIV virus.

The present invention also relates to a method for preventing and/or treating a condition caused by the infection of an individual with a HIV virus, comprising a step of administering, to an individual in need thereof, an effective amount of a vaccine composition as defined above.

DESCRIPTION OF THE FIGURES

FIG. 1A: results at Day 21 after the first injection; FIG. 1B: results at Day 35 after the first injection; FIG. 1C: results at Day 49 after the first injection.

FIG. 4 illustrates PE-Mean fluorescence of control wells. The measured PE fluorescence mean representing the density of NKp44L at the surface of the CD4+ T cells has been measured by cytofluotometry from the cells of the wells number 4 to number 1). The Y axis represents the X-mean fluorescence. The X axis represents the different controls. With (3S) or without (−) 3S16Nter peptides, and without (−) or with serum from anti-3S16Nter IgG negative (rabbit neg) or positive (rabbit pos) rabbits at the 1/50 dilution. Controls have been tested in duplicate and the Standard Deviations are reported (error bars).

FIG. 5 illustrates X-Mean fluorescence of test items wells. The measured PE fluorescence mean representing the density of NKp44L at the surface of the CD4+ T cells has been measured by cytofluotometry from the cells of the wells number 16 to number 45. The Y axis represents the X-mean fluorescence. The X axis represents the different tested conditions. All the wells were tested in the presence of 3S16Nter peptides. Serum from a rat vaccinated with adjuvanted CRM197-3S16Nter immunoconjugate (R122 d49) was tested. Each dilution was tested in triplicate, Standard Deviation are reported (error bars). Anti-3S16Nter IgG negative serum (negative control) was tested at the 1/50 dilution. Anti-3S16Nter IgG positive serum was tested at the 1/100, 1/400, 1/1600 and 1/6400 dilutions.

DETAILED DESCRIPTION OF THE INVENTION

Figure 1:
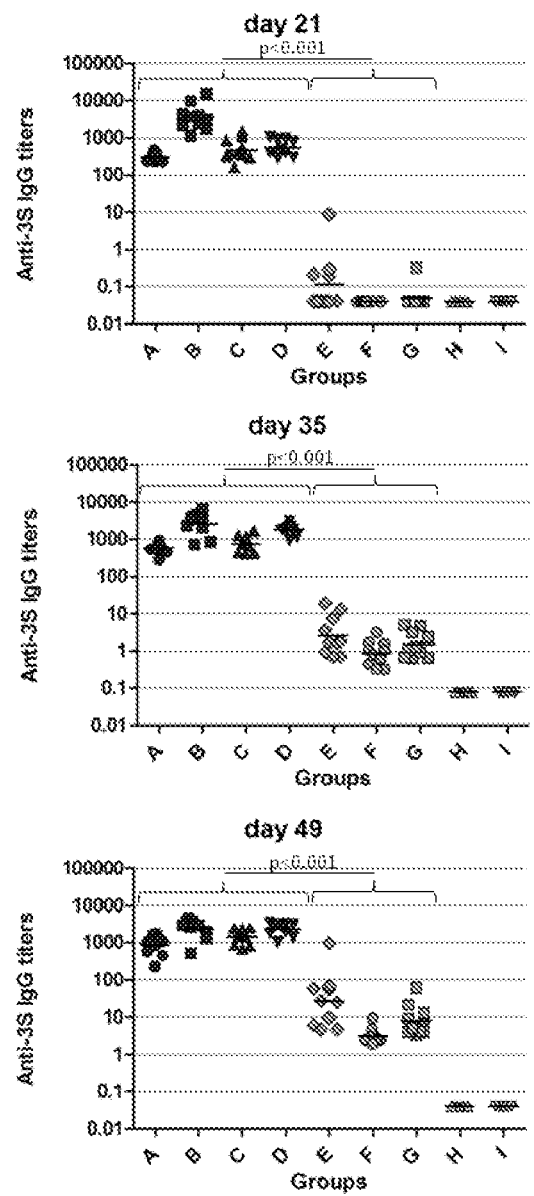
FIG. 1 illustrates the raising of anti-3S-peptide antibodies upon immunisation with 3S16Nter peptide conjugated with KLH or CRM197. Each symbol represents the results obtained from one mouse. Each bar represents the geometric mean value of the results obtained from the corresponding pool of mice. Abscissa: kind of composition used; Ordinate: anti-3S IgG titers as expressed in Arbitrary Units (A.U.). One Arbitrary Unit corresponds to the signal generated by a solution of the mouse monoclonal anti-3S antibody 15C8f2 at the final concentration of 1 ng/µl.
Figure 2:
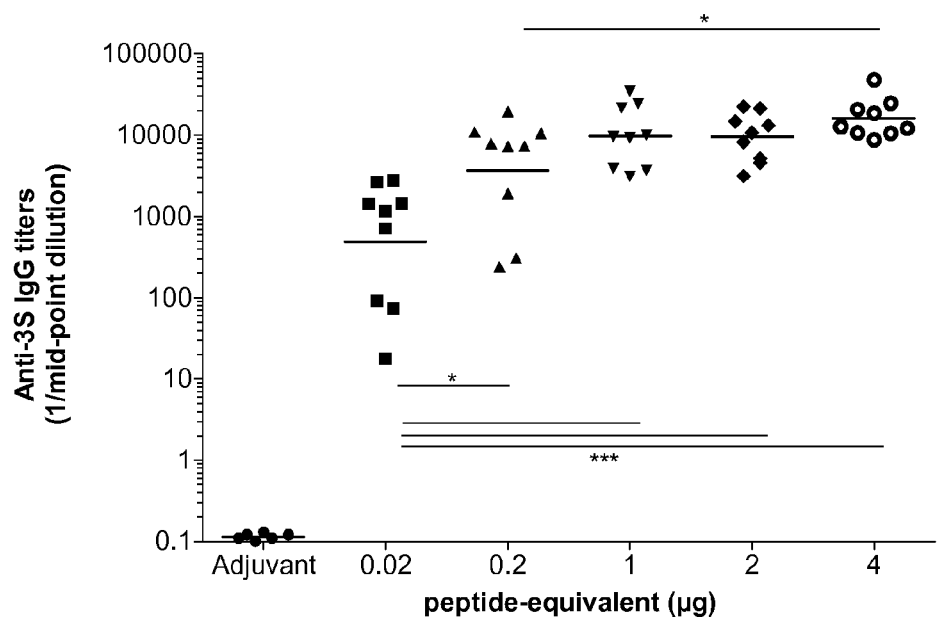
FIG. 2 illustrates the optimal 3S-peptide-CRM197 immuno-conjugate (3S drug substance) vaccine dose range in mice. Abscissa: dose of the immuno-conjugate as expressed as the amount of antigenic equivalent (respectively 0 ("Adjuvant"), 0.02 µg, 0.2 µg, 1 µg, 2 µg and 4 µg). Ordinate: Anti-3S16Nter IgG titers as expressed as 1/midpoint dilution). The mid-point dilution is the dilution of the antiserum giving half of the maximum signal. The X axis represents the different groups of mice vaccinated with increasing doses expressed in micrograms (µg) of 3S16Nter peptide equivalent of the 3S drug substance. Each symbol represents one mouse. A pool of serums from mice vaccinated with CRM197-3S immuno-conjugate is used to normalize the ELISA assay. Statistical significances calculated by a non-parametric Mann Whitney test are reported. *: $0.5 > p > 0.1$; : $0.1 > p > 0.01$; *: $p < 0.01$.
Figure 3:
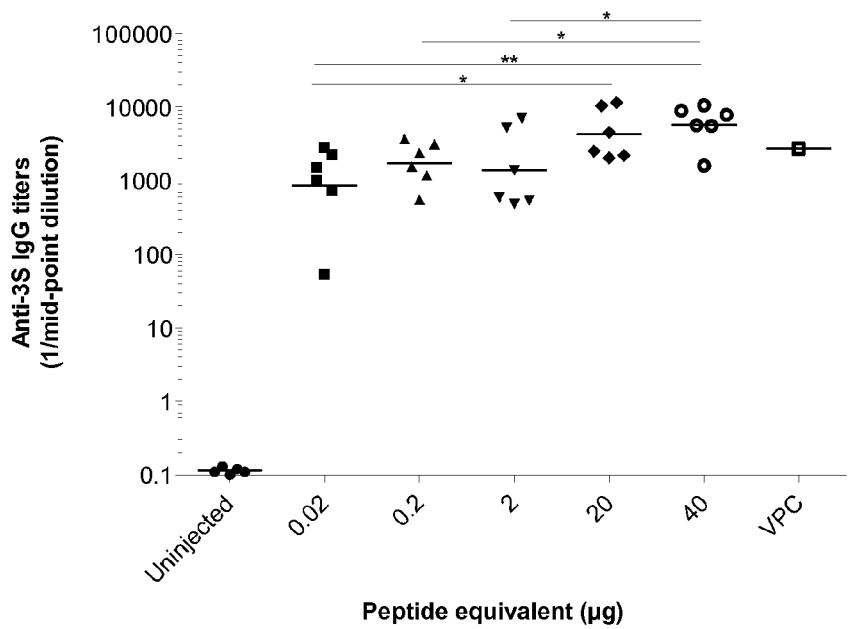
FIG. 3 illustrates the optimal 3S-peptide-CRM197 vaccine dose range in rats. Abscissa: dose of the immuno-conjugate (the 3S drug substance) as expressed as the amount of peptide conjugated to the carrier without taking into account the weight of the carrier and the weight of the linker (peptide-equivalent) (respectively 0 ("Adjuvant"), 0.02 µg, 0.2 µg, 1 µg, 2 µg and 4 µg). Ordinate: Anti-3S16Nter IgG titers as expressed as 1/mid-point dilution). The mid-point dilution is the dilution of the antiserum giving half of the maximum signal. The X axis represents the different groups of rats vaccinated with increasing doses expressed in micrograms (µg) of peptide-equivalent of the 3S -drug substance. Each symbol represents one rat. A pool of serums from rats vaccinated with 20 µg and 50 µg of CRM197-3S immuno-conjugate formulated with aluminium hydroxide is used to normalize the ELISA assay. Statistical significances calculated by a non-parametric Mann Whitney test are reported. *: $0.5 > p > 0.1$; : $0.1 > p > 0.01$; *: $p < 0.01$

The present invention primarily provides for a novel immunogenic compound useful for preparing compositions, and especially vaccine compositions against HIV.

The inventors have performed a thorough research work in view of designing an immunogenic compound endowed with the ability to induce a high and efficient antibody response against a 3S peptide.

As used herein, a 3S peptide is collectively defined in the present specification as a peptide of formula (I) which is described below. A 3S peptide encompasses the 3S peptide of SEQ ID No 5 ($NH_2$-CPWNASWSNKSLDDIW-COOH) which is known in the art.

As used herein, anti-3S antibodies consist of antibodies directed against a peptide of formula (I) and include antibodies directed against the 3S peptide of SEQ ID No 5.

The 3S peptide of SEQ ID No 5 was previously identified as a candidate anti-HIV antigen by Vieillard et al. (Vieillard et al., 2008, PNAS, Vol. 105 (6): 2100-2104). It is reminded that Vieillard et al. have induced anti-3S antibodies by using an immuno-conjugate compound consisting of 3S peptides of SEQ ID No 5 that have been covalently linked to the well-known KLH carrier protein.

It is herein reminded that KLH is almost the sole carrier protein which is presently used in vaccine compositions comprising immunogenic substances under the form of antigen-protein carrier conjugates. Moreover KLH has been widely used for generating antibodies (Lee, Huang, Lasanthi, Jayathilaka, Lateef and Gupta, 2010. Production of antipeptide antibodies, Methods in Molecular Biology, 657: 93-108, S.D. Schwartzbach and T. Osafune (eds.), Springer; Ragupathi, Gathuru and Livington, 2005, Antibody inducing polyvalent cancer vaccines, Cancer Treat Res, 123:157-150; Harris and Markl, 1999, Keyhole limpet hemocyanin (KLH): a biomedical review, Micron, 30-597-623).

Surprisingly, the inventors have found that the KLH conventional carrier protein used by Vieillard et al. was not suitable for designing an immunogenic compound raising an efficient anti-3S antibody response aimed at inducing a protective effect against the immunological disorders caused by the infection of an individual with a virus of the HIV family, and particularly a HIV-1 virus. Notably, the inventors have unexpectedly found that 3S peptide-grafted KLH molecules (KLH-3S) formed aggregates, which led to an heterogenous final immunogenic compound comprising associated entities of various apparent molecular weights. Thus, the inventors have found that an immunogenic compound comprising KLH-3S conjugates cannot be reproducibly manufactured with the aim of obtaining a chemically defined product usable as a medicament, and especially as a medicament for human use.

Highly surprisingly, the inventors have found that an efficient anti-3S antibody response may be obtained by using a specific immunogenic compound consisting of an antigen-carrier conjugate wherein the carrier molecule consists of a CRM197 protein. Notably, it has been found that an approximately 100 fold increase in the anti-3S antibody is obtained by using CRM197 as the carrier protein, as compared with an immunogenic compound wherein the same antigenic peptide is covalently bound to the conventional KLH carrier protein.

The CRM197 protein consists of a non-toxic mutant of the well-known diphtheria toxin, which mutant was initially described by Uchida et al. (1973, J. Biol. Chem., Vol. 248 : 3838-3844). The CRM197 mutant protein was initially described as the translation product of the mutant tox97 gene where a G→A transition led to the substitution of the glycine (G) residue at position 52 of the wild-type diphtheria toxin with a glutamic acid residue (E).

According to the applicant's knowledge, CRM197 has been poorly used until now as a carrier molecule for preparing immunogenic compounds, especially for peptide conjugation. According to the applicant's knowledge, CRM197 has been used exclusively as a carrier substance for oligosaccharide antigens, i.e. for raising antibodies against non-protein structures that are well known in the art to possess a very specific immunological behaviour. Even more precisely, it appears that CRM197 has been exclusively used as a carrier molecule for (i) oligosides derived from the capsular antigens of *Streptococcus pneumoniae*, (ii) oligosides from *Neisseria menigitidis* and (iii) for the capsular polysaccharide of *Haemophilus* influenza type B.

The present invention relates to an immunogenic compound comprising a peptide of the following formula (I)

$$NH_2\text{-}[Nt]_y\text{-}P\text{-}W\text{-}N\text{-}X_1\text{-}S\text{-}X_2\text{-}S\text{-}N\text{-}X_3\text{-}X_4\text{-}X_5\text{-}X_6\text{-}X_7\text{-}I\text{-}W\text{-}[Ct]_z\text{-}COOH \quad (I),$$

wherein:
y is an integer meaning 0 or 1,
z is an integer meaning 0 or 1,
Nt consists of a peptide having from 1 to 100 amino acids in length,
Ct consists of a peptide having from 1 to 100 amino acids in length, $X_1$ is an amino acid selected from the group consisting of A (Alanine), T (threonine), S (Serine) and N (Asparagine),
$X_2$ is an amino acid selected from the group consisting of W (Tryptophane) and A (Alanine),
$X_3$ is an amino acid selected from the group consisting of K (Lysine) and R (Arginine,
$X_4$ is an amino acid selected from the group consisting of S (Serine) and T (Threonine),
$X_5$ is an amino acid selected from the group consisting of L (Leucine), Y (Tyrosine) and Q (Glutamine),
$X_6$ is an amino acid selected from the group consisting of D (Aspartic acid), N (Asparagine), E (Glutamic acid), S (Serine), G (Glycine) and K (Lysine),
$X_7$ is an amino acid selected from the group consisting of D (Aspartic acid), Q (Glutamine), L (Leucine), A (Alanine), K (Lysine) and E (Glutamic acid), which peptide of formula (I) is covalently linked to a carrier protein consisting of a CRM 197 protein.

For the purpose of the present description, the immunogenic compound of formula (I) may also be termed herein $$NH_2\text{-}[Nt]_y\text{SEQ ID No 1-}[Ct]\text{-}COOH \quad (I)$$

In some embodiments of the immunogenic compound of formula (I), $X_1$ preferably means A,
In some embodiments of the immunogenic compound of formula (I), $X_2$ preferably means W,
In some embodiments of the immunogenic compound of formula (I), $X_3$ preferably means K,
In some embodiments of the immunogenic compound of formula (I), $X_4$ preferably means S,
In some embodiments of the immunogenic compound of formula (I), $X_5$ preferably means L,
In some embodiments of the immunogenic compound of formula (I), $X_6$ preferably means D, and
In some embodiments of the immunogenic compound of formula (I), $X_7$ preferably means D.

In some embodiments of the immunogenic compound of formula (I), one or more of the amino acids selected from the group consisting of $X_1$, $X_2$, $X_3$, $X_4$, $X_5$, $X_6$ and $X_7$ have their respective preferred meaning specified above. In some embodiments, 1, 2, 3, 4, 5, 6 or 7 of the amino acids selected from the group consisting of $X_1$, $X_2$, $X_3$, $X_4$, $X_5$, $X_6$ and $X_7$ have their respective preferred meaning specified above.

In the embodiments wherein the seven amino acids selected from the group consisting of $X_1$, $X_2$, $X_3$, $X_4$, $X_5$, $X_6$ and $X_7$ have their respective preferred meaning specified above, then the said immunogenic peptide consists of the peptide of formula (IIa):

$$NH_2\text{-}[Nt]_y\text{-}P\text{-}W\text{-}N\text{-}A\text{-}S\text{-}W\text{-}S\text{-}N\text{-}K\text{-}S\text{-}L\text{-}D\text{-}D\text{-}I\text{-}W\text{-}[Ct]\text{-}COOH \quad (IIa),$$

which may also be termed:

$$NH2\text{-}[Nt]y\text{-}SEQ ID No 2\text{-}[Ct]z\text{-}COOH \quad (IIa).$$

In the embodiments wherein the six amino acids selected from the group consisting of $X_1$, $X_3$, $X_4$, $X_5$, $X_6$, and $X_7$ have their respective preferred meaning specified above, and wherein the amino acid $X_2$ means A (Alanine), then the said immunogenic peptide consists of the peptide of formula (IIb):

$$NH_2\text{-}[Nt]_y\text{-}P\text{-}W\text{-}N\text{-}A\text{-}S\text{-}A\text{-}S\text{-}N\text{-}K\text{-}S\text{-}L\text{-}D\text{-}D\text{-}I\text{-}W\text{-}[Ct]_z\text{-}COOH \quad (IIb),$$

which may also be termed:

$$NH_2\text{-}[Nt]y\text{-}SEQ ID No 6\text{-}[Ct]z\text{-}COOH \quad (IIb)$$

A Nt peptide having from 1 to 100 amino acid residues in length encompasses peptides having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 amino acid residues in length.

In some embodiments, a Nt peptide has 10 amino acid residues in length or less, which encompasses an amino acid length of 5 amino acid residues or less.

In some embodiments, the N-terminal residue of a Nt peptide consists of a C (Cysteine) residue.

In some embodiments, the Nt peptide is of the following formula (III):

$$NH_2—C-Y_1-T-Y_2-V-(III) \text{ of SEQ ID No 3,}$$

wherein:
Y$_1$ is an amino acid selected from the group consisting of T (Threonine) and P (Proline),
Y$_2$ is an amino acid selected from the group consisting of A (Alanine), T (Threonine) and N (Asparagine).

In some other embodiments, the Nt peptide consists of one cysteine residue (also termed "C").

A Ct peptide having from 1 to 100 amino acid residues in length encompasses peptides having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 amino acid residues in length/

In some embodiments, a Ct peptide has 10 amino acid residues in length or less, which encompasses an amino acid length of 5 amino acid residues or less.

In some embodiments, the C-terminal residue of a Ct peptide consists of a C (Cysteine residue).

In some embodiments, the Nt peptide is of the following formula (IV):

$$-Y_3-Y_4-M-T-W-COOH \text{ (III) of SEQ ID No 4,}$$

wherein:
Y$_3$ is an amino acid selected from the group consisting of D (Aspartic acid), Q (Glutamine), E (Glutamic acid) and N (Asparagine), and
Y$_4$ is an amino acid selected from the group consisting of N (Asparagine), H (Histidine), S (Serine) and K (Lysine).

In some other embodiments, the Ct peptide consists of one cysteine residue (also termed "C").

In some other embodiments, the Ct peptide is absent in an immunogenic compound of the invention.

In some specific embodiments of an immunogenic compound according to the invention, the said peptide is of the formula (V) described below.

Thus, the present invention relates to an immunogenic compound comprising a peptide of the following formula (V)

$$NH_2\text{-}(A1)_m\text{-SEQ IDNo 1-}(A2)_n\text{-COOH} \qquad (V),$$

wherein:
m is an integer meaning 0 or 1,
n is an integer meaning 0 or 1,
A1 is an amino acid residue, and
A2 is an amino acid residue,
which peptide of formula (V) is covalently linked to a carrier protein consisting of a CRM 197 protein.

In some embodiments of a peptide of formula (V), m is equal to 1, n is equal to 0 and A1 means a Cysteine (C) residue.

The present invention also relates to an immunogenic compound comprising a peptide of the following formula (VIa)

$$NH_2\text{-}(A1)_m\text{-SEQ IDNo 2-}(A2)_n\text{-COOH} \qquad (VIa),$$

wherein:
m is an integer meaning 0 or 1,
n is an integer meaning 0 or 1,
A1 is an amino acid residue, and
A2 is an amino acid residue,
which peptide of formula (VIa) is covalently linked to a carrier protein consisting of a CRM 197 protein.

The present invention also relates to an immunogenic compound comprising a peptide of the following formula (VIb)

$$NH_2\text{-}(A1)_m\text{-SEQ IDNo 6-}(A2)_n\text{-COOH} \qquad (VIb),$$

wherein:
m is an integer meaning 0 or 1,
n is an integer meaning 0 or 1,
A1 is an amino acid residue, and
A2 is an amino acid residue,
which peptide of formula (VIb) is covalently linked to a carrier protein consisting of a CRM 197 protein.

In some embodiments of a peptide of formula (VIa) or (VIb), m is equal to 1, n is equal to 0 and A1 means a Cysteine (C) residue.

As it is readily apparent, peptides of formulae (V), (VIa) or (VIb) are specific embodiments of a peptide of formula (I) according to the invention. Thus, every embodiment of an immunogenic compound of the invention which is described with a reference to a peptide of formula (I) encompasses the same embodiment where the peptide of formula (I) consists of a peptide of formula (V) or a peptide of formula (VIa) or (VIb), unless otherwise specified.

As it is also readily apparent, peptides of formulae (VIa) or (VIb) are specific embodiments of a peptide of formula (V) according to the invention. Thus, every embodiment of an immunogenic compound of the invention which is described with a reference to a peptide of formula (I) or of formula (V) encompasses the same embodiment where the peptide of formula (I) or of formula (V) consists of a peptide of formula (VIa) or (VIb), unless otherwise specified.

As used herein, amino acid residues encompass Alanine (also termed "A" or "Ala"), Arginine (also termed ("R" or "Arg"), Asparagine (also termed "N" or "Asn"), Aspartic acid (also termed "D" or "Asp"), Cysteine (also termed "C" or "Cys"), Glutamine (also termed "Q" or Gln"), Glutamic acid (also termed ("E" or "Glu"), Glycine (also termed "G" or "Gly"), Histidine (also termed "H" or "His"), Isoleucine (also termed "I" or "Ile"), Leucine (also termed "L" or "Leu"), Lysine (also termed "K" or "Lys"), Methionine (also termed "M" or "Met"), Phenylalanine (also termed ("F" or "Phe"), Proline (also termed "P" or "Pro"), Serine (also termed "S" or "Ser"), Threonine (also termed "T" or "Thr"), Tryptophan (also termed "W" or "Trp"), Tyrosine (also termed "Y" or "Tyr") and Valine (also termed "V" or "Val").

As specified previously, CRM197 is a non-conventional carrier molecule for protein antigen presentation to the cells of the immune system. CRM197 is easily available to the one skilled in the art. CRM197 is notably commercialized under reference CRM197 (rDNA) by Company Pfenex Inc (San Diego, USA). CRM197 is defined as the protein of SEQ ID No 8 herein.

A peptide of formula (I), including its specific embodiments of formula (V) and of formulae (VIa) or (VIb), as described herein can be produced by a known cloning technology or by chemical synthesis.

For example, DNA encoding a peptide of formula (I) is prepared by use of a cloning technology, and inserted into an autonomously replicable vector to prepare a recombinant DNA. The recombinant DNA is introduced into an appropriate host, such as Escherichia coli, Bacillus subtilis, Actinomyces, yeast, filamentous fungus, a plant cell, an insect cell and an animal cell, to obtain a transformant. From the cultured product of the transformant, a peptide containing a peptide of formula (I) can be obtained. Alternatively, DNA encoding a peptide of formula (I) is prepared and subjected to an acellular protein-synthesis system using wheat germ and a cell extract from Escherichia coli, to synthesize the peptide of the invention. In some embodiments where the peptide of formula (I) is linked to a carrier protein, then an immunogenic product consisting of a fusion protein containing both a peptide of formula (I) and the desired carrier protein may be synthesized by a recombinant DNA technique.

Moreover, using a customary chemical synthesis method for a peptide of formula (I), such as a "solid phase method" or "a liquid phase method", amino acids are successively connected and extended by dehydration/condensation.

For manufacturing an immunogenic compound as defined above, any suitable conjugation reaction can be used, with any suitable linker where necessary, which are well known by the skilled person.

In certain embodiments of a peptide of formula (V), (VIa) or (VIb), the amino acid residues A1 and/or A2 are absent, when the integers m and/or n is(are) equal to 0, respectively.

In some embodiments of a peptide of formula (V), (VIa) or (VIb), A1 is present (i.e. the integer m=1) and A2 is absent (i.e. the integer n=0)

In some embodiments of a peptide of formula (V), (VIa) or (VIb), A1 is absent (i.e. the integer m=0) and A2 is present (i.e. the integer n=1).

In some preferred embodiments of a peptide of formula (V), (VIa) or (VIb), A1 and/or A2, when present, consist(s) of a cysteine residue.

In some preferred embodiments of a peptide of formula (V), (VIa) or (VIb), A1 is present and consists of an N-terminal cysteine residue and A2 is absent, i.e. the integer n is equal to 0. In these preferred embodiments, the peptide or formula (V), or (VIa) consists of the peptide of SEQ ID No 5. In these preferred embodiments, the peptide of formula (V) or (VIb) consists of the peptide of SEQ ID No 7.

On a technical point of view, peptides of formula (I), including peptides of formula (V) or of formula (VI), above may be covalently linked to CRM197, either directly or through a linker moiety, through their N-terminal end amino acid residue or through their C-terminal end amino acid residue. In these general embodiments, the covalent linkage may involve an available alpha-amino group or alpha-carboxy group of the said amino acid residue from a peptide of formula (I). Alternatively, the covalent linkage may involve an available amino group, carboxy group or thiol group located on a lateral chain of the said amino acid residue from a peptide of formula (I).

However, it has been found herein that an immunogenic compound as defined above wherein the peptides of formula (I) are covalently linked to CRM197 through their C-terminal end is not optimal, since such an immunogenic peptide has a propensity to form aggregates, which may represent a significant drawback for obtaining a chemically defined and easily reproducible pharmaceutical composition.

Thus, in some preferred embodiments of an immunogenic compound as defined above, the peptides of formula (I) are covalently bound to CRM197 through their N-terminal end.

Further, in an immunogenic compound as defined above, peptides of formula (I) are covalently linked to CRM197 most preferably through an appropriate linker agent. It has been found herein that the presence of a linker agent bridging peptides of formula (I) and CRM197 introduces some flexibility in the molecule, thus allowing a better availability of the relevant epitopes contained in the peptides of formula (I) to the corresponding receptors present at the surface of the cells of the immune system, i.e. mainly T cells and B cells.

Thus, in some preferred embodiments of an immunogenic compound as defined above, peptides of formula (I) are covalently bound to CRM197 through a linker moiety.

In some preferred embodiments, peptides of formula (I) are covalently bound to CRM197 by their N-terminal end, through a linker moiety.

The said linker moiety is obtained by reacting a linker agent both with CRM197 and peptides of formula (I).

In preferred embodiments, the linker agent possesses two distinct reactive groups, (i) a succinimidyl group and (ii) a maleimide group, respectively. Each of the reactive group is available for reaction with an amino group or a thiol group of (i) CRM197 and of (ii) a peptide of formula (I), respectively.

Such kind of linker agent is very well known in the art and is easily commercially available.

However, it has been found herein that some of these heterobifunctional linker agents are not optimal, especially when the manufacture of a vaccine composition is sought. Illustratively, the inventors have found that the use of a heterobifunctional linker agent like MBS (m-Maleimido-Benzoyl-N-hydroxySuccinimidyl ester) led to a final product that was very poorly water-soluble. A low water-solubility of an immunogenic compound may consist of a substantial technical drawback in view of manufacturing a vaccine composition, since the final forms of vaccine compositions that are ready to be administered usually consist of water-based saline liquid solutions or suspensions which may eventually also contain one or more pharmaceutically acceptable water-soluble solvents. As illustrated in the examples herein, an immuno-conjugate wherein CRM197 is covalently linked to peptides of formula (I) through MBS remains immunogenic, i.e. able to raise relevant anti-3S antibodies when injected in vivo, despite its inability to be used as the active ingredient of a vaccine composition, due to its propensity to form aggregates.

Surprisingly, the inventors have determined that a restricted family of linker agents is the most appropriate for manufacturing an immunogenic compound as defined herein which shall be fully water-soluble, and thus which shall be homogenously distributed throughout the whole volume of a liquid composition with the view of being eligible as the immunogenic active ingredient of a vaccine composition. The said restricted family of linker agents encompasses, or even consists of, the linker agents named SMPB and sulfo-SMPB, respectively.

Thus, in some preferred embodiments of an immunogenic compound as defined above, the said linker agent is selected form the group consisting of SMPB (succinimidyl 4-[p-maleimidophenyl]butyrate) and Sulfo-SMPB (sulfosuccinimidyl 4-[p-maleimidophenyl]butyrate).

Methods for conjugating two proteins with a linker agent in general, and more particularly with a linker agent selected from the group consisting of SMPB and Sulfo-SMPB, are well known by the one skilled in the art. Illustratively, such protocols are disclosed in the leaflets that are made publicly available by the Pierce Company (Illinois, Etats-Unis).

SMPB and Sulfo-SMPB consist of heterobifunctional linker agents that contain both a N-hydroxysuccinimide (NHS) ester group and a maleimide group. Conjugation using SMPB or Sulfo-SMPB is usually performed by a two-step procedure. In a first step, the amine-containing protein (e.g. CRM197) is reacted with a several-fold molar excess of the linker agent at pH 7-9 to form amide bonds, followed by removal of excess non-reacted linker agent, usually by desalting or dialysis. In a second step, the sulfhydryl-containing molecule (e.g. peptide of formula (I)) is added to react with the maleimide groups already attached to the first protein (e.g. free maleimide groups of the linker chain that is already covalently linked to CRM 197) at pH 6.5-7.5 to form stable thioether bonds.

Using SMPB or Sulfo-SMPB as linker agents for covalently linking peptides of formula (I) to CRM197 carrier protein leads to a conjugate of formula (VII) below:

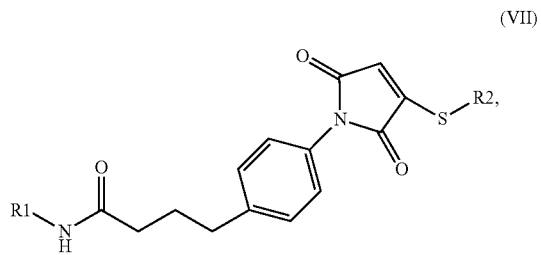

(VII)

wherein:

- R1 consists of one reactive group of CRM197, and wherein the NH group attached thereto derives from (i) the alpha amino group located at the N-terminal end of CRM197 or (ii) a lateral chain amino group from a Lysine (K) amino acid residue of CRM197
- R2 consists of a peptide of formula (I), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

As it is known in the art, the CRM197 protein comprises a plurality of reactive groups R1, so that a plurality of peptides of formula (I) may be linked to CRM197 in a conjugate of formula (VII).

Thus, most preferred embodiments of an immunogenic compound as defined above are those wherein a plurality of reactive groups of CRM197 are covalently linked to a peptide of formula (I) having SEQ ID No 5 or SEQ ID No 7, which peptide possesses a cysteine residue at its N-terminal end, according to the covalent linkage represented by formula (VII) above.

In some embodiments of an immunogenic compound as defined above, a mean number of peptides of formula (I) ranging from 2 to 20 are covalently linked to one molecule of CRM197. In preferred embodiments, a mean number of from 5 to 10 peptides of formula (I), which includes a mean number of from 7-8 peptides of formula (I), are covalently linked to one molecule of CRM197.

This invention also relates to compositions comprising an immunogenic compound as defined above, in combination with one or more immunoadjuvant substances.

A composition as defined herein which comprises an immunogenic compound as defined above, and which further comprises one or more immuno-adjuvant substances, may also be termed an “immunogenic composition” or alternatively a “vaccine composition” in the present specification.

In some embodiments, there is no substantial distinction to be made between an immunogenic composition according to the invention and a vaccine composition according to the invention, beyond the terms employed to designate such compositions, excepted that the features of the vaccine composition shall comply with the technical requirements of the various Drug agencies for the grant of marketing authorizations for human or veterinary use. Instead, an immunogenic composition according to the invention may not comply to the requirements of Drug agencies while being usable for administration to animals, e.g. for producing anti-3S antibodies that may be of further use, including a further use as a detection or a diagnostic reagent.

More precisely, an immunogenic composition is aimed at generating antibodies directed against a peptide of formula (I) when it is administered to a mammal organism, e.g. a mouse, a rabbit, a sheep, a horse or a goat organism, in situations wherein the generated antibodies are not expected to exert a preventive or a therapeutic effect in the immunized mammal organism. Immunogenic compositions according to the invention may be used for producing antibodies directed against a peptide of formula (I), for a further non-therapeutic use of these antibodies, e.g. as a HIV-1 virus detection reagent or a HIV-1-derived peptide detection reagent.

On another hand, a vaccine composition according to the invention is aimed at generating antibodies directed against a peptide of formula (I) in the mammal organism to which the said vaccine composition is administered, in situations wherein the generated antibodies are expected to exert a preventive or a therapeutic effect in the immunized mammal organism.

Thus, compositions according to the invention encompass both (i) immunogenic compositions and (ii) vaccine compositions. Further, immunogenic compositions and vaccine compositions may differ in the type of auxiliary substances, including immuno-adjuvant substances and excipients that are contained therein. An immunogenic composition according to the invention may raise an anti-3S antibody production in an animal, including animals that are not at risk regarding an infection by a HIV virus, for which no preventive nor a therapeutic effect is sought. A vaccine composition according to the invention is aimed, in the individual who has been administered therewith, at raising the production of anti-3S antibodies that will exert a preventive or a therapeutic effect against an infection by a HIV virus, especially a protective effect against the CD4+ T cell decline in HIV-infected individuals, which causes a decrease of the pathogenicity of the virus.

In some embodiments of an immunogenic composition or of a vaccine composition as defined herein, an immunoadjuvant may be selected form the group consisting of (i) mineral salts, (ii) emulsions, (iii) microbial natural or synthetic derivatives, (iv) combination adjuvants, (v) cytokine-derived or accessory molecules-derived adjuvants, and (vi) particulate formulations.

A list of suitable immunoadjuvants is described in the Table hereunder.

| Adjuvant/formulations |
| --- |
| Mineral salts |
| Aluminum salts (hydroxide, phosphate) (Alum) <br> Calcium phosphate |
| Emulsions |
| MF59 (Microfluidized detergent stabilized squalene oil-in-water emulsion) <br> Incomplete Freund's adjuvant (IFA, stabilized water/Drakeol oil) <br> Montanide ISA-51 (Stabilized water-in-oil emulsion) and ISA-720 <br> (stabilized water/squalene) |
| Microbial (natural and synthetic) derivatives |
| Monophosphoryl lipid A (MPL) <br> Detox (MPL + CWS) <br> OM-174 (Lipid A derivative, *E. coli*), OM-triacyl <br> Modified LT, CT (Genetically modified bacterial toxins [heat-labile enterotoxin, cholera toxin] to provide non-toxic adjuvant effect) <br> CpG ODN (synthetic oligonucleotides containing immunostimulatory CpG motifs) |
| Combination Adjuvants |
| AS04 (Alum + MPL) <br> AS02 (Oil-in-water emulsion + MPL + QS-21) <br> AS01(Liposomes + MPL + QS21) |
| Immuno-adjuvants |
| Cytokines: (IL-2, IL-12, GM-CSF, Flt3) <br> Accessory molecules (B7.1) |
| Particulate formulations |
| Liposomes (DNPC/Chol) <br> DC Chol (Lipoidal immunomodulators able to self-organize into liposomes) <br> Virosomes ™ (Unilamellar liposomal vehicles, immunostimulating reconstituted influenza virosomes [IRIV]) <br> ISCOMS ® (structured complex of saponins and lipids) <br> PLA (polylactic acid) <br> PLG (poly[lactide-co-glycolide]) microparticles <br> Proteosomes ™ |

Immunoadjuvants comprising mineral salts are preferably selected from the group consisting of (1) aluminium salts, preferably of formula $KAl(SO_4)_2$, 12 $H_2O$, and (2) calcium phosphate.

Emulsion-based immunoadjuvants are preferably selected from the group consisting of (1) MF59, which is a microfluidized detergent stabilized squalene oil-in-water emulsion, (2) incomplete Freund's adjuvant, also termed IFA, (3) Montanide ISA 51 which is a water-in-oil stabilized emulsion, (4) and (4) ISA-720 which is a stabilized composition comprising water and squalene.

Immuno-adjuvants comprising natural or synthetic microbial derivatives are preferably selected from the group consisting of (1) monophosphoryl lipid A (MPL) (e.g. from Corixa, Hamilton, Mont., USA) (2) Detox (MPL+CWS), which consists of an oil droplet emulsion of monophosphoryl lipid A and mycobacterial cell wall skeleton, (3) OM-174, which is a soluble adjuvant derived from *Escherichia coli* lipid A, (4) non-toxic bacterial toxins, preferably modified toxins, such as the heat labile toxin from *E. coli*, the cholera toxin, and in particular the B subunits thereof (termed LTB and CTB, respectively), and (5) CpG ODN which are synthetic oligonucleotides containing immunostimulatory CpG motifs.

Combination adjuvants are preferably selected from the group consisting of (1) AS04 which is a combination of alum and monophosphoryl lipid A (MPL), (2) AS02 which is an oil-in-water emulsion comprising a combination of monophosphoryl lipid A (MPL) and QS-21 (e.g. from Aquila Biopharmaceuticals, Inc., Framingham, Mass., USA), and (3) AS01 which is consists of a liquid suspension of liposomes with two immunostimulant components: 3'-O-desacyl-4'-monophosphoryl lipid A (MPL) and *Quillaja saponaria* 21 (QS-21).

Cytokine-derived or accessory molecules-derived adjuvants are preferably selected from the group consisting of (1) cytokines such as IL-2, IL-12 (e.g. from Genetics Institute, Cambridge, Mass., USA), GM-CSF (e.g. from Hoffman La-Roche, Basel, Switzerland) and Flt3 and (2) accessory molecules like B7.1

Particulate formulations are preferably selected from the group consisting of (1) liposomes such as liposomes of DNPC/Chol, or DC Chol, the latter consisting of lipoid immunomodulators that are able to self-organize into liposomes, (2) Virosomes™ which are unilamellar liposomal vehicles, immunostimulating reconstituted influenza virosomes [IRIV], (3) ISCOMS® which are structured complex of saponins and lipids, (4) polylactic acid (PLA) and poly[lactide-co-glycolide] (PLG microparticles, and (5) Proteosomes™.

The immunoadjuvant compounds or compositions described above are easily available to the one skilled in the art, notably because they are commercially available.

However, the inventors have found that, when using specifically an immunogenic compound as defined herein, an efficient antibody response is obtained, i.e. an antibody response having an order of magnitude which complies with a preventive or a therapeutic effect in human individuals, when the said immunogenic compound is combined with aluminium hydroxide ($Al(OH)_3$) as the immuno-adjuvant substance. Aluminium hydroxide-based immuno-adjuvant substance consists of a particulate material under the form of a colloidal suspension having a particle size distribution of about 1-10 μm with a mean particle size of about 2-3 μm (Lindblad, 2004, Immunology and Cell Biology, Vol. 82: 497-505).

Noticeably, the inventors have found that other highly conventional immuno-adjuvant substances, including especially the well-known immuno-adjuvant aluminium phosphate, allow the induction of lower anti-3S peptide antibody titer levels, as compared to aluminium hydroxide, which antibody titer levels may be useful for producing antibodies as laboratory reagents but are too much low for an endogenous production of anti-3S antibodies able to exert a preventive or therapeutic medical effect.

Thus, in preferred embodiments of a composition according to the invention, the said immuno-adjuvant substance consists of aluminium hydroxide.

Further, the inventors have found that, for obtaining an optimal anti-3S antibody response, aluminium hydroxide shall be used in preferred conditions to avoid aggregation of the $Al(OH)_3$ particles and ensure an homogenous distribution of these particles in the final liquid suspension.

According to the invention, it has been found that formation of aluminium hydroxide particle aggregates may be avoided, or at least substantially delayed or reduced, when the final ready-to-use composition comprises 100-200 mM NaCl and 0.5-2.0 mM sodium phosphate, and most preferably 150 mM NaCl and 1 mM sodium phosphate. According to this embodiment, the rate of aluminium hydroxide particles aggregation is highly minimized, without altering the ability of the particles to adsorb the immunogenic compound, which specific conditions enhance the ability of the composition for raising an efficient protective anti-3S peptide antibody production.

Thus, in some embodiments of a composition according to the invention, the said composition is adapted to form a ready-to-use vaccine composition comprising a final concentration of aluminium hydroxide ranging from 0.1 mg/mL to 5 mg/mL, preferably from 0.05 mg/mL to 2 mg/mL, and is most preferably of about 1 mg/mL, as expressed as $Al^{3+}$ ions content. According to the European Pharmacopoeia, the amount of aluminium adjuvant should be less than 1.25 mg of aluminium per dose and 850 µg of aluminium per dose in the United States (according to the Code of Federal Regulations)

Also, according to certain embodiments of a composition according to the invention, the said composition is adapted to form a ready-to-use vaccine composition comprising a final concentration of 0.1 mM to 50 mM sodium phosphate, preferably 0.5 mM to 15 mM sodium phosphate, and most preferably around 1 mM sodium phosphate.

In a specific aspect, a composition according to the invention is adapted to form a ready-to-use vaccine composition comprising an amount of the said immunogenic compound ranging from 0.01 µg to 200 µg per dosage unit as expressed in antigenic peptide equivalent, preferably from 0.05 µg and 50 µg per dosage unit, and most preferably from 0.1 µg to 20 µg per dosage unit.

As used herein, an amount of an immunogenic compound expressed as "antigenic peptide equivalent" consists of the amount of peptides of formula (I) that is contained in the considered immunogenic compound material. According to the invention, the amount of peptides of formula (I) which are linked to one molecule of CRM197 is measured preferably by Amino Acid Analysis. This method is the methodology conventionally used to determine the amino acid composition of proteins. Proteins are macromolecules consisting of covalently bonded amino acid residues organized as a linear polymer. The peptide bonds are broken upon incubation under acid condition leading to the release of amino acids. An amino acid analysis is then performed on the product of the hydrolysis.

According to the present invention, Amino Acid Analysis is preferably used to determine the rate of coupling of peptide of formula (I) on CRM197. This was possible since some amino acids are both present on CRM197 and the grafted peptides and other such as F (Phenylalanine) are only present on CRM197. Based on the results of the amino acids present only on CRM197 and of those present both on CRM197 and the peptide of formula (I) conjugated thereto, a calculation allowed to determine the coupling ratio of the peptide of formula (I) onto CRM197.

Typically, after hydrolysis of the conjugate between CRM197 and peptides of formula (I), the amino acids present in the test samples are separated by reverse phase high pressure liquid chromatography (RP-HPLC). Usually, this instrument has a pre- or post-column derivatization capability and the detector is an ultraviolet-visible or fluorescence detector depending on the derivatization method used. An integrator is used for the transforming the analog signal from the detector and for quantitation of each amino acid. (Amino acid analysis of peptide loading ratios in conjugate vaccines: a comparison of electrochemical detection and 6-aminoquinolyl-N-hydroxysuccinimidyl carbamate pre-column derivatization methods Nahas D D et al Bioconj Chem 2008 Jan. 19(1) 322-6 Epub 2007 dec 12). The amount of peptides of formula (I) which are linked to one molecule of CRM197 can also be measured by mass spectrometry analysis.

A composition according to the invention may be in liquid or solid forms.

In some embodiments, a composition according to the invention consists of a liquid suspension, either as a liquid suspension concentrate or as a ready-to-use liquid suspension.

In other embodiments, a composition according to the invention consists of a solid particulate material (i.e. the conjugate), which includes especially a lyophilized material and has to be put into contact with the adjuvant and other excipients prior to the injection.

This invention also pertains to a vaccine composition comprising an immunogenic compound as defined above, or a composition as defined above, with one or more pharmaceutically acceptable carriers.

The formulation of such immunogenic compositions is well known to persons skilled in the art. Immunogenic compositions of the invention preferably include a pharmaceutically acceptable carrier. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. The preparation and use of pharmaceutically acceptable carriers is well known in the art. Except insofar as any conventional media or agent is incompatible with the active ingredient, use thereof in the immunogenic compositions of the present invention is contemplated.

Such immunogenic compositions can be administered parenterally, e.g., by injection, either subcutaneously or intramuscularly, as well as orally or intranasally and other mucosal routes. Other modes of administration employ oral formulations, pulmonary formulations, suppositories, and transdermal applications, for example, without limitation. Oral formulations, for example, include such normally employed excipients as, for example, pharmaceutical grades of mannitol, lactose, starch, magnesium stearate, sodium saccharine, cellulose, magnesium carbonate, and the like, without limitation.

It is shown in the examples herein that a composition comprising an immunogenic compound as defined above in combination with the appropriate immuno-adjuvant substance and with the appropriate pharmaceutically acceptable excipient(s) induces, when administered to an individual, the production of high titers of anti-3S peptide IgG antibodies.

Importantly, the examples herein show that the anti-3S peptide antibodies found in the serum of individuals immunized with a composition according to the invention inhibit the expression of NKp44L at the surface of CD4+ T cells in a dose-dependent manner.

As it is known in the art, the inhibition of NKp44L expression at the surface of CD4+ T cells causes a protective effect on the CD4+ T cells decline by decreasing NK cell activation and NK cell cytotoxicity towards CD4+ T cells in HIV-infected individuals.

The present invention also concerns the immunogenic compound as defined above, or the composition as defined above, for use as a medicament.

This invention also relates to the immunogenic compound as defined above, or the composition as defined above, for use for preventing and/or treating a condition caused by the infection of an individual with a HIV virus.

As used herein, preventing or treating an infection of an individual with an HIV-1 virus encompasses (i) preventing or treating a disease linked to an infection of the said individual with an HIV-1 virus, including AIDS and (ii) preventing progression of HIV-1 disease.

As used herein, the term "HIV infection" generally encompasses infection of a host animal, particularly a human host, by the type 1 human immunodeficiency virus (HIV-1). "HIV-1" can be used herein to refer to any strains, forms, subtypes, clades and variations in the HIV-1 family. Thus, treating HIV-1 infection will encompass the treatment of a person who is a carrier of any of the HIV-1 family of retroviruses or a person who is diagnosed of active AIDS, as well as the treatment or prophylaxis of the AIDS-related conditions in such persons. A carrier of HIV-1 may be identified by any methods known in the art. For example, a person can be identified as an HIV-1 carrier on the basis that the person is anti-HIV-1 antibody positive, or is HIV-1-positive, or has symptoms of AIDS. That is, "treating HIV-1 infection" should be understood as treating a patient who is at any one of the several stages of HIV-1 infection progression, which, for example, include acute primary infection syndrome (which can be asymptomatic or associated with an influenza-like illness with fevers, malaise, diarrhea and neurologic symptoms such as headache), asymptomatic infection (which is the long asymptomatic period with a gradual decline in the number of circulating CD4+ T cells), and AIDS (which is defined by more serious AIDS-defining illnesses and/or a decline in the circulating CD4 cell count to below a level that is compatible with effective immune function). In addition, "treating or preventing HIV-1 infection" will also encompass treating suspected infection by HIV-1 after suspected past exposure to HIV-1 by e.g., contact with HIV-1-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or thereafter.

The term "treating HIV-1 infection" should also be understood in the context of anti-retroviral therapies, whether the patients are totally responsive or partially responsive to such therapies in terms of viral load and/or CD4 T cell count.

The term "preventing HIV-1 infection" may encompass treating a person who is free of HIV-1 infection but is believed to be at risk of infection by HIV-1, sooner or later.

The term "treating AIDS" means treating a patient who exhibits more serious AIDS-defining illnesses and/or a decline in the circulating CD4+ T cell count to below a level that is compatible with effective immune function. The term "treating AIDS" also encompasses treating AIDS-related conditions, which means disorders and diseases incidental to or associated with AIDS or HIV-1 infection such as AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia *purpurea* and associated opportunistic infections such as *Pneumocystis carinii* pneumonia, Mycobacterial tuberculosis, esophageal candidiasis, toxoplasmosis of the brain, CMV retinitis, HIV-related encephalopathy, HIV-1-related wasting syndrome, etc.

Thus, the term "preventing AIDS" as used herein means preventing in a patient who has HIV-1 infection or is suspected to have HIV-1 infection or is at risk of HIV-1 infection from developing AIDS (which is characterized by more serious AIDS-defining illnesses and/or a decline in the circulating CD4+ T cell count to below a level that is compatible with effective immune function) and/or AIDS-related conditions.

Thus, the terms "preventing progression of HIV-1" as used herein means preventing in a patient who has an HIV-1 infection, the decrease of its CD4+ T cell count and/or preventing the increase of its viral load, the two main markers linked to the complication of the disease and to an increase severity of the disease.

The invention also deals with the use of the immunogenic compound as defined above, or the composition as defined above, for preparing a vaccine composition for preventing and/or treating a condition caused by the infection of an individual with a HIV virus.

The present invention also pertains to a method for preventing and/or treating a condition caused by the infection of an individual with a HIV virus, comprising a step of administering, to an individual in need thereof, an effective amount of a vaccine composition as defined in the instant specification.

The present invention is further illustrated by, without being limited to, the examples hereafter.

EXAMPLES

Example 1

Preparation of an Immunogenic Compound and Determination of Some of their Properties A. Preparation of Immunogenic Compounds The following immunogenic compounds or conjugates were synthesized. There were derived from KLH and CRM197 using either MBS or SMPB as crosslinker molecules. The used peptide was the 3S peptide consisting of SEQ ID No 2 with either an additional cysteine residue at its amino-terminus end or at its carboxy-terminus end.

CRM197-MBS-Nter(Cys)-3S
CRM197-SMPB-Nter(Cys)-3S
CRM197-SMPB-Cter(Cys)-3S
KLH-MBS-Nter(Cys)-3S For the sake of clarity, the peptide which is termed "Nter(Cys)-3S" above consists of the 3S peptide of SEQ ID No 5 herein.

Two heterobifunctional cross-linkers were tested: sulfo-SMPB (Sulfo-(Succinimidyl-4-(p-maleimidophenyl) Butyrate) and sulfo-MBS (Sulfo-(m-Maleimidobenzoyl-N-hydroxysuccinimide) ester). These molecules consist of a maleimide moiety linked by a polyethylene chain to an ester of N-hydroxysuccinimide (Cross-linking of protein by w-maleimido alkanoyl N-hydroxysuccinimido esters. Partis M. D and al. Journal of Protein Chemistry, vol. 2, No 3, 1983). The succinimide moiety can react with amino groups of the protein. Once this reaction has occurred, the maleimide moiety reacts with sulfhydryl groups of the 3S peptides. They are different in length, 7.3 Å for sulfo-MBS and 11.6 Å for sulfo-SMPB. The linker elimination and buffer exchange were made by size exclusion chromatography (SEC).

The coupling reaction was a two-step reaction. The first step was the activation of the CRM197 with the cross-linker. 15 milligrams of linker, diluted in dimethyl sulfoxide were added to 20 milligrams of CRM197 in a volume of 5-20 ml of conjugation buffer (PBS 10 mM pH7-pH7.4) and mixed gently for 30-90 min at room temperature (Protective immunogenicity of two synthetic peptides selected from the amino acid sequence od *Bordetella pertussis* toxin subunit S1. Askelöf P. and al. PNAS, vol. 87, pp 1347-1351, February 1990). This reaction was followed by a purification of the activated CRM197 by SEC (PD 10 column (GE Healthcare, Chalfont St. Giles United Kingdom) or Bio-Gel P2 column (Biorad Marnes-1a-Coquette, France)). Secondly, the activated CRM197 and the 3S-derived peptide were mixed for 30 min-2 hours at room temperature allowing the covalent coupling of the peptide onto the activated CRM197. To block unreacted maleimido groups of activated CRM197, cystein-HCl (SIGMA, Missouri, USA) is added in excess to the solution after the conjugation reaction (A practical approach to crosslinking Mattson G. and al. Molecular Biology Reports 17: 167-183, 1993). This step limited the creation of multimers. The immuno-conjugates were then purified by size exclusion chromatography. The immuno-conjugates were analyzed using an amino acid analysis (AAA) to determine the peptide/CRM197 ratio. The CRM197-3S peptide was lyophilized with a lyoprotector (Lyophilisation and development of solid protein pharmaceuticals. Wang W. International Journal of Pharmaceutics 203 (2000) 1-60; Fundamentals of freeze-drying. Nail S. L and al. Pharm Biotechnol. 2002; 14:281-360).

B. Properties of these Immunogenic Compounds

Surprisingly, all immuno-conjugates obtained and corresponding to the 3S peptide of SEQ ID No 2 with the Cys at the C-terminal end, the CRM197 carrier and SMPB or MBS as a linker, were not soluble in water or in 0.9% NaCl solution, even after a long time, with heating or shaking. As these immuno-conjugates were not suitable to obtain an homogeneous and reproducible substance, these compounds have not been tested in animal.

Surprisingly, the immuno-conjugates using the 3S peptide of SEQ ID No 2 with the Cys at the N-terminal end, the CRM197 carrier and MBS as a linker were not soluble in water or in 0.9% NaCl solution, even after a long time, with heating or shaking Even though these immuno-conjugates were not suitable to obtain a homogeneous and reproducible compound, these compounds were tested in the mouse.

Surprisingly the immune-conjugate corresponding to the 3S peptide of SEQ ID No 2 with the Cys at the N-terminal end, the CRM197 carrier and SMPB as a linker were found spontaneously soluble in water or in 0.9% NaCl solution. Such immuno-conjugates were further studied.

Example 2

Comparative Assays

A. Materials and Methods
A.1. The various immuno-conjugate compounds tested in Example 2 have been prepared as disclosed in Example 1.
A.2. The various compositions tested are disclosed in Table 1 below.

A.3. Animals

Animals were BALB/cJ females provided by Charles River Laboratories (Lyon, France) which were 8 weeks-old at day 0 of the experiment.

A.4. Method of administration

Each of the compositions described in Table 1 was injected to mice by the subcutaneous route at a dose of 40 µg, as expressed as the amount of antigenic peptide equivalent.

Mice were injected subcutaneously with 100 µl of each composition tested at Day 0, Day 14 and Day 28, respectively.

The weight of each mice was followed-up at day 0, 14, 35 and 49, respectively.

A.5. ELISA assay

The ELISA assay was designed to perform the measurement of IgG antibodies that would recognized the peptides of SEQ ID No 2, also called anti-3S16Nter peptides. The anti-3S16Nter IgG antibody titers were determined by an Enzyme-Linked ImmunoSorbent Assay (ELISA) A pool of serums from rats vaccinated with 20 or 50 µg/vaccination of 3S16Nter peptide equivalent of the immuno-conjugate s reported in Table 1 at day 0, day 14 and day 28 was used to normalize the values between different 96-well plates.

Eight dilutions of the day 49 serums are tested (from 1/50 to 1/150, 1/450, 1/1350, 1/4050, 1/12150, 1/36450, and 1/109350). The antigen coated to the Nunc Maxisorp micro plates is a 3S16Nter peptide conjugated to bovine serum albumin (BSA) with a different linker than the one used for the synthesis of the immuno-conjugate s: SMCC (succinimidyl-4-(N-maleimidomethyl)cyclohexane-1-carboxylate) (produced from Imject® Maleimide Activated BSA Protein Kits purchased from Thermo Fisher Scientific, Waltham, USA). The anti-3S16Nter IgG antibodies are revealed by a colorimetric reaction using a goat anti-rat IgG (Fc), conjugated to the HorseRadish Peroxydase (HRP) (Jackson Immunoresearch, West Grove, USA), and the HRP substrate: the tetramethylbenzidine (TMB) (Sigma, Missouri, USA).

B. Results

IgG titers of anti-3S antibodies were measured by the ELISA assay described in the Materials and Methods section.

The results are depicted in FIG. 1.

The results of FIG. 1 show that the immuno-conjugate compounds comprising KLH as the carrier protein (E, F and G) induce a very low anti-3S antibody production, as compared with the immuno-conjugate compounds comprising CRM197 as the carrier protein (A, B, C and D) at Day 21 (FIG. 1A), Day 35 (FIG. 1B) and Day 49 (FIG. 1C), respectively.

TABLE 1

| Groups | A | B | C | D | E | F | G | H | I |
|---|---|---|---|---|---|---|---|---|---|
| N= | 10 | 10 | 10 | 10 | 10 | 10 | 10 | 5 | 5 |
| Carrier | CRM197 | CRM197 | CRM197 | CRM197 | KLH | KLH | KLH | — | — |
| Peptide | 3S16Nter | 3S16Nter | 3S16Nter | 3S16Nter | 3S16Nter | 3S16Nter | 3S16Nter | — | — |
| Crosslinker | SMPB | MBS | SMPB | MBS | MBS | MBS | MBS | — | — |
| Adjuvant | Adjuphos | Adjuphos | Alhydrogel | Alhydrogel | IFA | Alhydrogel | Adjuphos | Alhydrogel | Adjuphos |

The peptides of SEQ ID No 5 is also named anti-3S16Nter peptide.
SMPB and MBS were purchased from PIERCE (Illinois, USA) or SIGMA (Missouri, USA).
Adjuphos ® 2% (aluminium phosphate gel) was purchased from Brenntag (Frederikssund, Denmark). Adjuphos ® was used at a final concentration of 3 mg/ml of $Al^{3+}$ ions, which final concentration is adapted to the administration of 300 µg of $Al^{3+}$ ions per injection.
Alhydrogel ® 2% (aluminium hydroxide gel) was purchased from Brenntag (Frederikssund, Denmark). Alhydrogel ® was used at a final concentration of 3 mg/ml of $Al^{3+}$ ions, which final concentration is adapted to the administration of 300 µg of $Al^{3+}$ ions per injection.
Incomplete Freund's adjuvant (IFA) was purchased from SIGMA (Missouri, USA). IFA was emulsified with the immuno-conjugate compound by vortexing during one hour a mixture of 50 µl of IFA with 50 µl of the aqueous immuno-conjugate solution.

The results of FIG. 1 also show that the immuno-conjugate compounds obtained by using MBS (B and D) as the linker agent possess good immunogenic properties, despite that they are poorly usable, due to their ability to form heterogenous suspension containing an increasing amount of aggregates with an increasing time of storage. Immuno-conjugate present in compound A and C present good immunogenic properties as well. For reason of clarity it is from now on called the "3S drug substance".

The results of FIG. 1 also show that the compositions containing Adjuphos® as the immuno-adjuvant substance (A, B) possess immunogenic properties of the same order as the compositions containing Alhydrogel® as the immuno-adjuvant substance, despite the fact that compositions with Adjuphos® tend to form aggregates and thus consist of a final product having difficult handling properties.

Example 3

Optimisation of the Formulation of the Immuno-Conjugate

Adsorption of antigen to aluminium salts is critical for the adjuvant effects and formulation of the vaccine antigens, especially salts, is an important element of the potential interaction between aluminium and the antigen. Aluminium hydroxide surface is composed of hydroxyl groups coordinated to aluminium. The surface charge of the phosphate aluminium is composed of both hydroxyl and phosphate groups. The adsorption of proteins by aluminium adjuvant is a complex process and involves contribution of electrostatic, hydrophobic ant other attractive forces.

The aim of these formulation studies was to obtain a vaccine preparation with a homogeneous and opalescent aspect, without visible aggregates after gentle shaking. The target of the study was to obtain a formulation that would adsorb at least 95% of the 3S drug substance onto the aluminium particles after one hour of incubation.

In first exploratory studies, the 3S drug substance was mixed with the aluminium hydroxide adjuvant in 135 mM sodium chloride and 0.5 mM sodium phosphate. Aggregates were observed but almost 100% of the 3S drug substance was adsorbed onto the aluminium salts. When aluminium phosphate was used, the mix led to a homogeneous solution but only 80% of the 3S drug substance was adsorbed onto the aluminium salts. A screening of formulations was performed. The different physico-chemical parameters were tested: pH, sodium chloride concentration and phosphate concentration. Adsorption studies were performed in suspensions containing 1 mg/mL of aluminium ions. 37.5 µg of proteins (corresponding to 12.5 µg of pep.eq) were mixed to the adjuvant suspension to produce a final volume of 0.250 mL using low adsorption tubes. In the formulation with aluminium hydroxide the pH was adjusted to pH7.2 with phosphate anions. The preparation was gently mixed. Preliminary experiments indicated that adsorption was completed in few minutes. The suspension was centrifuged and the clear supernatant analysed for protein. The antigen concentration of the supernatant was determined using micro protocols of the bicinchoninic acid protein assay (Pierce, Rockford, Ill., USA). The procedure in microplate was followed. Absorbencies were measured at 562 nm.

The effect of adding phosphate anions to the formulation was studied in order to avoid aggregates. It may be possible to optimize the surface charge of aluminium in relation to the antigen by pretreating the adjuvant with phosphate anions. This treatment may result in the adsorption of basic proteins by electrostatic attractive forces. Phosphate anions are also included in the vaccine preparation to control the pH.

The effect of ionic strength was also investigated. The addition of sodium chloride to increase the ionic strength to 250 mM improved the adsorption rate. Using aluminium hydroxide, the aspect of the formulation was improved by phosphate anions addition in the preparation.

Two formulations giving consistently a homogeneous and opalescent aspect were obtained:

Formulation 1: 7 mM Sodium phosphate, 135 mM Sodium chloride, aluminium hydroxide at 1 mg/mL of $Al^{3+}$ ions pH 7

Formulation 2: 15 mM Sodium phosphate, 135 mM Sodium chloride, aluminium hydroxide at 1 mg/mL of $Al^{3+}$ ions pH 7

Using aluminium phosphate, these formulations were homogeneous and opalescent but the adsorption capacity did not reach the target of 95%. In contrast aluminium phosphate, additional phosphate anions increased the negative surface charge. Thus treatment of aluminium phosphate with phosphate anions is not expected to change the type of protein, i.e. basic, which is adsorbed. We modified the surface charge of aluminium phosphate adjuvant by decreasing the pH with a pretreatment of aluminium phosphate adjuvant with HCl. When the pH of the adjuvant formulation was decreased to 5.5, an adsorption of 100% was obtained. The following formulation 3 was therefore selected:

Formulation 3: 150 mM sodium chloride, aluminium phosphate at 1 mg/mL of $Al^{3+}$ ions pH 5.5

The three formulations exhibited similar immunogenicity in mouse. Formulation 1, at 1 mg/mL of $Al^{3+}$ ions, 7 mM sodium phosphate and 135 mM Sodium chloride, pH 7 was selected, to limit the effect of the phosphate anions on adsorption during aging.

The optimization of the formulation continued. The sodium phosphate and sodium chloride concentrations were changed to obtain a formulation acceptable according to the two criteria: close to 100% adsorption and homogeneous/opalescent aspects. To obtain an isotonic preparation, the concentration of sodium chloride was increased to 150 mM. Since the phosphate anions can affect the adsorption onto the surface of aluminium hydroxide, the concentration was decreased to 1 mM in the preparation. The formulation with aluminium hydroxide at the concentration of 1 mg/mL of $Al^{3+}$ ions with 1 mM sodium phosphate and 150 mM sodium chloride pH 7,2 was selected (formulation 4: 1 mM Sodium phosphate, 150 mM Sodium chloride, aluminium hydroxide at 1 mg/mL of $Al^{3+}$ ions pH 7.2). Finally, after different experiments (formulation and stability testing), the pH 6.8 was chosen, compatible with the pH of the adjuvant and of the 3S drug substance (formulation 5: 1 mM Sodium phosphate, 150 mM Sodium chloride, aluminium hydroxide at 1 mg/mL of $Al^{3+}$ ions pH 6.8).

Formulation 5 has been selected for the above reasons (immunogenicity, good adsorption of the immuno-conjugate onto aluminium hydroxide, opalescent aspect, compliance for use in human—pH—isotonicity selected for use in humans.

The 3S drug substance formulated in formulation 5 is denominated from now on "VAC-3 S".

Example 4

Determination of Optimal Dose Ranges

This example describes the amount of the 3S drug substance that can be injected into humans, according to immune response of the said 3S drug substance candidate in mice and rats.

A. Methods

Two dose-range finding studies have been performed in the mouse BalB/CByJ (Charles River Laboratories, Lyon, France) and in the rat CD® IGS (Charles River Laboratories, Lyon, France) with the 3S drug substance or CRM197-3S16Nter in order to determinate the maximal human dose to be used during the first-in-man trial. The tested formulation is in aluminium hydroxide (1 mg/mL of $Al^{3+}$ ions, 150 mM sodium chloride and 3.6 mM sodium phosphate. In the described experiments, the 3S drug substance has been tested with 3.6 mM sodium phosphate because of a too high concentration of sodium phosphate in the tested lot of the -3S drug substance. The drug product, namely "VAC-3S", is formulated in 1 mM sodium phosphate instead of 3.6 mM sodium phosphate. Adsorption of the 3S drug substance on aluminium hydroxide is equivalent between 1 and 3.6 mM phosphate. Moreover, a bridging experiment of immunogenicity will be performed between VAC-3S and the 3S drug substance formulated with 3.6 mM sodium phosphate. In clinical trials, the schedule of administration is three vaccinations at one month apart. In mice and rats, the same schedule was performed with three vaccinations but at fourteen days apart. The anti-3S16Nter IgG titer was measured as the biological response to the 3S drug substance. Such antibodies are known to inhibit the interaction between 3S peptide and its receptor on human CD4+ T cells.

B. Determination of Optimal Dose Range in Mice

Six groups of 9 mice vaccinated with increasing doses of the 3S drug product: 0.02, 0.2, 1, 2, and 4 µg of 3S16Nter-peptide-equivalent of the 3S drug substance formulated in 150 mM sodium chloride, 3.6 mM sodium phosphate, and 1 mg/mL of aluminum hydroxide as adjuvant in a volume of 0.05 mL. One group of 6 mice has been vaccinated with the adjuvant alone.

The doses of 4, 2 and 1 µg of peptide equivalent induce not significantly different anti-3S16Nter IgG antibody titers.

Hence, the plateau of the immune response (circulating anti-3S16Nter IgG antibody titers) induced by the 3S drug substance starts at a value included between 0.2 and 1 µg of 3S16Nter-peptide equivalent in the mouse, after three monosite vaccinations of 0.05 mL of adjuvanted 3S drug substance two weeks apart.

C. Determination of Optimal Dose Range in Rats

Five groups of 6 rats were vaccinated with increasing doses of the 3S drug product: 0.02, 0.2, 2, 20 and 40 µg of 3S16Nter-peptide-equivalent of the drug substance formulated in 150 mM sodium chloride, 3.6 mM sodium phosphate, and 1 mg/mL of aluminium hydroxide as adjuvant in a volume of 0.5 mL per vaccination. One group of 6 rats was not vaccinated as negative control.

A vaccination with 40 µg of peptide-equivalent results in significant higher anti-3S16Nter IgG titers (geometric mean=1/5776) than with 2 µg of peptide-equivalent (geometric mean=1/1413, p=0.03), than with 0.2 µg of peptide-equivalent (geometric mean=1/1736, p=0.02) and than with 0.02 µg of peptide-equivalent (geometric mean=1/861, p=0.009).

A vaccination with 40 µg of peptide-equivalent results in not significantly different anti-3S16Nter IgG antibody titers than a vaccination with 20 µg of peptide-equivalent (geometric means: 1/5776 and 1/4284 respectively, p=0.70).

Hence, the plateau of the immune response (circulating anti-3S16Nter IgG antibody titers) induced by the drug substance starts at a value included between 2 and 20 µg of 3S16Nter-peptide equivalent in the rat, after three injections of adjuvanted 3S drug substance two weeks apart.

D. Determination of Optimal Dose Range in Human

The rationale we used is that the adjuvanted 3S drug substance dose needed to obtain the anti-3S16Nter IgG antibody titer plateau in the mouse would correspond to the tenth of the dose needed to obtain the anti-3S 16Nter IgG antibody titer plateau in humans. This means that the plateau of the anti-S16Nter IgG would be attained in human between 2 (10 time 0.2 µg) and 10 µg (10 time 1 µg) of 3S16Nter-peptide equivalent.

We considered that the adjuvanted 3S drug substance dose needed to obtain the anti-3S16Nter IgG antibody titer plateau in the rat would correspond to the same dose needed to obtain the anti-3S16Nter IgG antibody titer plateau in humans.

Consequently, according to the dose-range finding performed in the mouse, the plateau of the immune response in humans could be expected to be attained at a minimal dose of adjuvanted 3S drug substance included between 2 and 10 µg of 3S16Nter-peptide equivalent.

According to the dose-range finding performed in the rat, the plateau of the immune response in humans could be expected to be attained at a minimal dose of adjuvanted 3S drug substance included between 2 and 20 µg of 3S16Nter-peptide equivalent.

The maximal human dose of the adjuvanted 3S drug substance to be injected in humans was set at 10 µg of 3S16Nter peptide-equivalent per vaccination, when formulated in 1 mg/ml of aluminium hydroxide, 150 mM sodium chloride and sodium phosphate buffer in 0.5 mL.

Therefore the dose to be used in human should be e.g. 10 µg of 3S16Nter peptide-equivalent per vaccination, and may preferably range between 0.1 and 20 µg of 3S16Nter peptide-equivalent per vaccination.

Example 5

Protective Effect of a Vaccine Composition

The aim of Example 5 was to test the ability of the antiserums of a rat vaccinated with the adjuvanted 3S drug substance to inhibit the expression of NKp44L at the surface of activated human CD4+ T cells induced by the 3S peptide, namely the 3S16Nter peptide.

CD4+ T cells were sorted from human PBMC and activated for 3 days with PHA (Thermo Fisher Scientific, Waltham, USA) then expanded for three days with recombinant IL-2 (Novartis, Horsham, United Kingdom). The cells were put in presence of 3S16Nter peptides (Covalab, Villeurbanne, France) in order to induce the expression of NKp44L at their surface.

The expression of NKp44L at the surface of the cells was measured using the intensity of a specific fluorescent staining measured by cytofluorometry.

The inhibition of NKp44L expression by the antiserums of vaccinated rat was studied.

The antisera were tested at different dilutions in triplicate.

A. Materials and Methods

Cells:

Human CD4+ T cells were obtained by magnetic separation from a leuko-platelet residue pouch ordered from the EFS ("Etablissement Francais du Sang").

The human CD4+ T cells were sorted from the pouch according to the following protocol:

1. The pouch is distributed in four Falcon tubes of 50 mL: 4×15 mL

2. Complete to 50 mL with RPMI1640+glutamax medium (ref 72400-054, GIBCO, Life Technologies, Carlsbad, USA)
3. Distribute the diluted blood in eight 50 mL tubes on 15 mL of Ficoll (Ref 17-829E, Eurobio, Les Ulis, France))
4. Centrifuge at 2800 rpm for 20 minutes without brake at room temperature.
5. Harvest the leucocytes rings and distribute them in four 50 mL tubes with a maximum of 25 mL per tube.
6. Complete the tube to 50 mL with RPMI1640 medium
7. Centrifuge at 2000 rpm, 7 minutes, room temperature
8. Discard the supernatant
9. Pool the pellets and wash in 50 mL of RPMI1640 medium, centrifuge at 1500 rpm for 5 minutes at room temperature.
10. Count the cells in trypan blue
11. 400 millions of PBMC are sorted
12. Wash the cells in 15 mL in the sorting buffer (PBS without Mg and Ca, 0.5% BSA, 2 mM EDTA). From that moment, cells are kept at 4° C. or in the ice in order to avoid the phagocytosis of the magnetic beads)
13. Add 10 µL of magnetic beads per $20 \times 10^6$ PBMCs=200 µL of magnetic beads suspension for 400 million of PBMC (MACS CD4 microbeads, Miltenyi Biotec, Paris, France)
14. Incubate for 30 minutes at 4° C.
15. Resuspend the cells in 1 mL of sorting buffer
16. Place two LS columns (Miltenyi Biotec, Paris, France) on a quadroMACS magnet (Miltenyi Biotec, Paris, France)
17. Equilibrate each of two LS columns with 3 mL of sorting buffer
18. Get the cellular suspension through the columns (0.5 mL in each column) by gravity
19. Wash two times each column with 5 mL of sorting buffer
20. Remove the columns from the magnet
21. Elute each column two times with 5 mL of sorting buffer, the first time by gravity, the second time using the piston.
22. Wash the eluted cells from each column in 15 mL of complete medium (RPMI1640+glutamax, 10% decomplemented SVF Gibco, Non Essential Amino Acids 100× (ref GIBCO, Life Technologies, Carlsbad, USA), Antibiotic/antimycotic (ref 15240-112, GIBCO, Life Technologies, Carlsbad, USA).
23. Count the cells in acetic blue.

The human CD4+ T cells were activated and expanded according to the following protocol:
1. 50 millions of CD4+ T cells were put in culture in 30 mL complete medium in a 75 cm2 (Ref 353136, Falcon, lieu, pays) flask vertically placed in a humid ventilated incubator at 37° C., 5% $CO_2$.
2. Add PhytoHemAgglutinine (PHA) at the final concentration of 1 µg/mL: 1 µL of an aliquot at 1 mg/mL per mL of medium. (PHA from Thermo Fisher Scientific, Waltham, USA)
3. After 3 days of PHA activation, add IL-2 (Aldesleukine, lieu, pays) at 100 UI/mL.

During the PHA activation and IL-2 expansion, the medium is changed by half when ever it becomes slightly yellow.

Test Items

Serums from a rat (*Rattus norvegicus*) Crl/CD(SD) were tested: This animal was vaccinated with 2 µg of 3S16Nter pep.eq./vaccination of 3S drug substance adjuvanted with aluminium hydroxide at day 0, day 14 and day 28. Its serum at day 49 was positive for anti-3S16Nter antibodies As a negative control, a pre-immune serum from the rat 482 was tested.

Controls

Positive control: The antiserum from the rabbit New Zealand (*Oryctolagus cuniculus*) from Charles River Laboratories, Lyon, France taken at day 49 was used as positive control at the 1/50 dilution. This rabbit was vaccinated at day 0, day 14 and day 28 with a CRM197-(3S16Nter) immunoconjugate adjuvanted with aluminium hydroxide, and its serum at day 49 was positive for anti-3S16Nter IgG.

Negative Control: The antiserum from a rabbit vaccinated with a non-relevant vaccine was used as a negative control at the 1/50 dilution

TABLE 2 identification number of the wells of the experiment control
Controls were tested in duplicate without or with 3S16Nter peptides.
Identification number of the wells and tubes are indicated in table 2 below.

|  | No serum | No serum | Control (−) | Control (−) | Control (+) | Control (+) |
|---|---|---|---|---|---|---|
| Without 3S16Nter | 4 | 5 | 8 | 9 | 12 | 13 |
| With 3S16Nter | 6 | 7 | 10 | 11 | 14 | 15 |

As the activation state of the CD4+ T cells that permits the expression of NKp44L in response to the exposure to 3S16Nter peptides in vitro is not known, all the controls have to be validated.

In order to validate the experiment, NKp44L must be expressed at the surface of the cells of the wells 6, 7, 10 and 11 and must not be expressed at the surface of the cells of the wells 4, 5, 8, 9, 12, 13, 14 and 15.

Protocol
1. The serums to test were tested in triplicate,
2. 20 µL of 1/40 dilution of a 3S16Nter peptide solution at 2 mg/mL: 25 µL of IVV-B122+975 µL of complete RPMI1640 medium. So 3S16Nter peptides were at a final concentration of 5 µg/mL,
3. 180 µL of the cellular suspension of CD4+ T cells from a flask.

For the 1/50 dilution of the serums, add 4 µL of the serums per well.
For the 1/100 dilution of the serums, add 8 µL of a 1/4 dilution of the serums.
For the 1/400 dilution of the serums, add 8 µL of a 1/16 dilution of the serums.
For the 1/1600 dilutions of the serums, add 8 µL of a 1/64 dilution of the serums.

TABLE 3 identification number of the wells of the rat serums
Rat serums were tested in triplicate in the presence of
3S16Nter pepties. Identification number of the wells and
tubes are indicated in the TABLE 3

| Serum | 482 | R122 | R122 | R122 | R122 |
|---|---|---|---|---|---|
|  | day 0 | day 48 | day 48 | day 48 | day 48 |
| Diluation | 1/50 | 1/50 | 1/100 | 1/400 | 1/1600 |
| With 3S16Nter | 31 | 34 | 37 | 40 | 43 |
| With 3S16Nter | 32 | 35 | 38 | 41 | 44 |
| With 3S16Nter | 33 | 36 | 39 | 42 | 45 |

3 wells are used as controls for the cytofluorometric analyse.

TABLE 4 identification number of the cytofluorometry control wells
In well 1, cells were not stained; in well 2, cells were put in presence
of the anti-IgM-PE antibody alone to assess the background;
in well 3, cells were stained with anti-CD4-APC alone.

| Antibody | Not stained | Anti-IgM PE alone | Anti-CD4-APC alone |
|---|---|---|---|
| With 3S16Nter | 1 | 2 | 3 |

4. The micro-plate is incubated for 4 hours in the cell incubator (37° C., humid atmosphere, 5% CO2).
5. Centrifuge the micro-plate for 5 min at 400 g.
6. Eliminate the supernant
7. Add 10 µL/well of the murine anti-NKp44L IgM 7.1+30 µL/well of PBS, 0.5% BSA (500 µL of antibody solution+ 1500 µL of PBS, BSA 0.5%) 8. Incubate for 1 hour at 4° C.
9. Add 150 µL/well of PBS, BSA 0.5%.
10. Centrifuge the micro-plate for 5 minutes at 400 g.
11. Eliminate the supernatant
12. Add 50 µL/well of a 1/25 dilution in PBS, 0.5% BSA of the secondary antibody anti-mouse IgM-PE.
13. Incubate for 30 minutes at 4° C.
14. Add 150 µL/well of PBS, BSA 0.5%.
15. Centrifuge the micro-plate for 5 minutes at 400 g.
16. Add 50 µL of a 1/25 dilution in PBS, 0.5% BSA of the anti-human CD4-APC antibody.
17. Transfer the cellular suspensions in FACS tubes.
18. Incubate for 15 minutes at room temperature.
19. Add 2 mL of PBS 1× per tube
20. Centrifuge for 5 minutes at 400 g
21. Add 300 µL of PBS 1×
22. Acquire the tubes at the cytofluorometer
Instrument SN: AN52257 Software version: Gallios
The number in bold corresponds to the well identification number.
Data are analysed the day of the analysis on the software Gallios and printed.
The results report the X-mean fluorescence of the PE marker of the cells
    Gated on the CD4+ T cells on a APC intensity/Forward Side Intensity dot plot
    Gated on the lymphocytes on a SSC intensity/Forward Side Intensity dot plot.
This X-mean value represents the density of NKp44L markers at the surface of CD4+ T cells.
B. Results

TABLE 5

| Well identification number (see table 2 & 3) | Serum | Dilution | 3S16Nter | PE X-mean fluorescence |
|---|---|---|---|---|
| 1 | None | NA | + | NA |
| 2 | None | NA | + | NA |
| 3 | None | NA | + | 0.4 |
| 4 | None | NA | − | 1.1 |
| 5 | None | NA | − | 1.1 |
| 6 | None | NA | + | 59.6 |
| 7 | None | NA | + | 64.7 |
| 8 | Rabbit anti-3S16Nter Ig Negative | 1/50 | − | 0.7 |
| 9 | Rabbit anti-3S16Nter Ig Negative | 1/50 | − | 0.8 |
| 10 | Rabbit anti-3S16Nter Ig Negative | 1/50 | + | 65.1 |
| 11 | Rabbit anti-3S16Nter Ig Negative | 1/50 | + | 61.3 |
| 12 | Rabbit anti-3S16Nter IgG Positive | 1/50 | − | 0.8 |
| 13 | Rabbit anti-3S16Nter IgG Positive | 1/50 | − | 1.1 |
| 14 | Rabbit anti-3S16Nter IgG Positive | 1/50 | + | 0.8 |
| 15 | Rabbit anti-3S16Nter IgG Positive | 1/50 | + | 0.8 |
| 31 | 482-d0 | 1/50 | + | 56.7 |
| 32 | 482-d0 | 1/50 | + | 58.6 |
| 33 | 482-d0 | 1/50 | + | 45.0 |
| 34 | R122-d49 | 1/50 | + | 0.6 |
| 35 | R122-d49 | 1/50 | + | 0.7 |
| 36 | R122-d49 | 1/50 | + | 0.7 |
| 37 | R122-d49 | 1/100 | + | 8.7 |
| 38 | R122-d49 | 1/100 | + | 13.6 |
| 39 | R122-d49 | 1/100 | + | 19.9 |
| 40 | R122-d49 | 1/400 | + | 57.7 |
| 41 | R122-d49 | 1/400 | + | 53.5 |
| 42 | R122-d49 | 1/400 | + | 27.3 |
| 43 | R122-d49 | 1/1600 | + | 56.4 |
| 44 | R122-d49 | 1/1600 | + | 49.4 |
| 45 | R122-d49 | 1/1600 | + | 56.0 |

Figure 4:
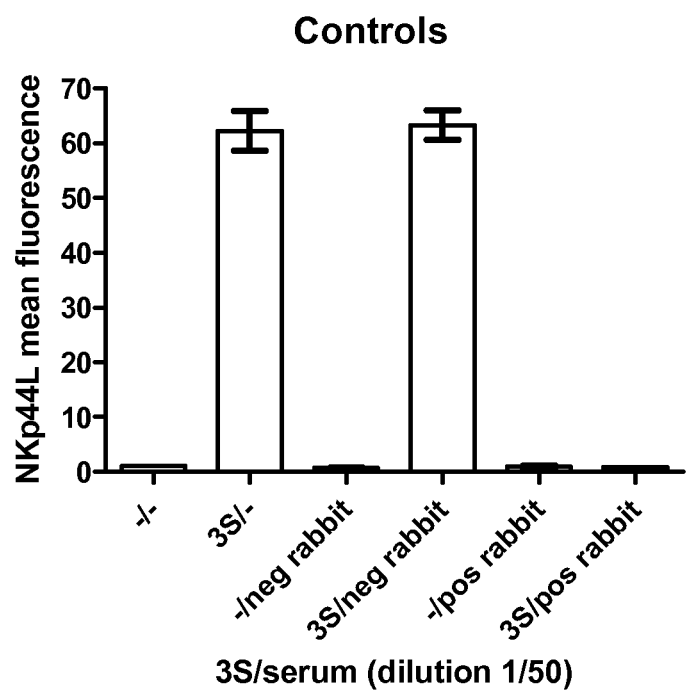
FIGS. 4 and 5 illustrate the ability of the anti-3S16Nter antibodies obtained after immunization of animals, including primates, with a 3S16Nter conjugated to carrier proteins (KLH or CRM197) as described herein.
Figure 5:
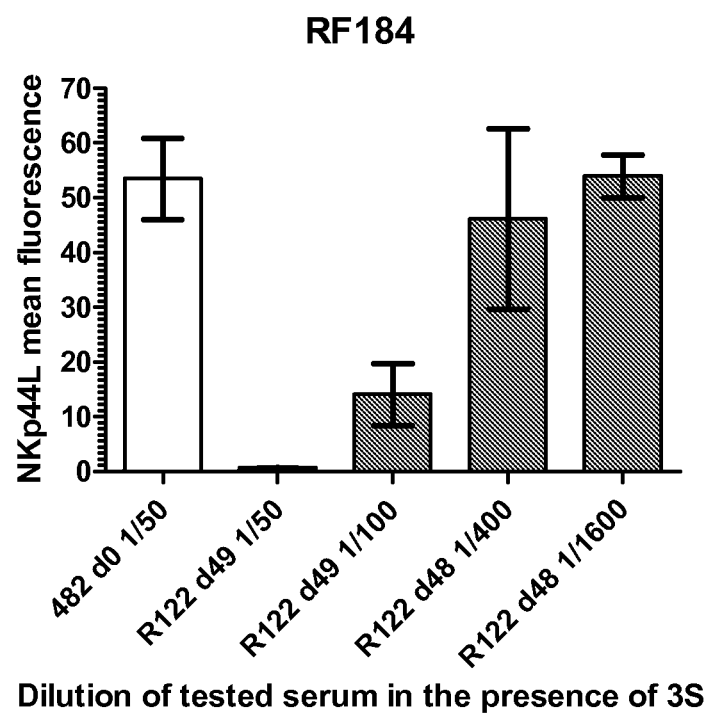

FIG. 4 depicts the PE-Mean fluorescence of control wells. The results obtained show that:
   In the wells without serum, without 3S16Nter peptides, the activated CD4+ T cells did not express NKp44L.
   In the wells without serum, in the presence of 3S16Nter peptides, the activated CD4+ T cells did express NKp44L at a mean level of 62.
   In the wells with rabbit anti-3S16Nter antibody negative serum at the 1/50 dilution, without 3S16Nter peptides, the activated CD4+ T cells did not express NKp44L.
   In the wells with rabbit anti-3S16Nter antibody negative serum at the 1/50 dilution, in the presence of 3S16Nter peptides, the activated CD4+ T cells did express NKp44L at a mean level of 63.
   In the wells with rabbit anti-3S16Nter antibody positive serum at the 1/50 dilution, with or without 3S16Nter peptides, the activated CD4+ T cells did not express NKp44L.
These results showed that the in vitro activated CD4+ T cells used in this experiment
   did not spontaneously express NKp44L at their surface,
   were capable of expressing NKp44L at their surface in response to an exposition to 3S16Nter peptides,
   that this expression was not induced nor inhibited by a non-relevant antiserum,
   that the surface of NKp44L was totally inhibited by an anti-3S16Nter IgG positive serum
Further, FIG. 5 depicts the results of the X-mean fluorescence of the test items wells.
The results obtained show that:
   In the wells with rat anti-3S16Nter antibody negative serums at the 1/50 dilution, in the presence of 3S16Nter peptides, the activated CD4$^+$ T cells did express NKp44L at a mean level of fluorescence of 53.
   In the wells with rat anti-3S16Nter antibody positive serums at the 1/50 dilution, in the presence of 3S16Nter peptides, the surface expression of NKp44L on activated CD4$^+$ T cells was totally inhibited.

In the wells with rat anti-3S16Nter antibody positive serums at the 1/100 dilution, in the presence of 3S16Nter peptides, the activated CD4' T cells did express NKp44L at a mean level of fluorescence of 14.

In the wells with rat anti-3S16Nter antibody positive serums at the 1/400 and 1/1600 dilutions, in the presence of 3S16Nter peptides, the surface expression of NKp44L on activated CD4+ T cells was not inhibited.

For summarizing Example 5, the results obtained show that, in an in vitro human cellular model of activated CD4+ T lymphocytes, the antisera of a rat vaccinated with the 3S drug substance adjuvanted with alhydrogel both highly inhibited the expression of NKp44L at the surface of the CD4+ T lymphocytes in a dose-dependent manner. This reflects the ability of these vaccine preparations to induce antibodies that can functionally block the effect of the 3S peptide on the NKp44L expression on CD4+ T lymphocytes.

Example 6

Preparation of Injectable Compositions and Method of Administration for Human Use Preparation of Vaccine:

VAC-3S is a sterile suspension for intramuscular injection containing the 3S drug substance adsorbed on aluminium hydroxide in buffered isotonic saline. The manufacturing of VAC-3S was performed in compliance with the GMP.

To obtain VAC-3S, the 3S drug substance is formulated at the concentration of 0.02 mg/mL of 3S16Nter peptide equivalent in 0.5 mL with aluminium hydroxide (1 mg/mL of $Al^{3+}$ ions) provided by Brenntag (Alhydrogel 85 2%-Ph Eur), 150 mM sodium chloride (European pharmacopoeia) and 1 mM sodium phosphate (European pharmacopoeia). Products for injection are used for the formulation of the vaccine. The final pH is at 6.8. VAC-3S contains no preservative.

Injections:

After shaking, the vaccine is a homogeneous white suspension ready to use. The vaccine could be injected intramuscularly in the deltoid. A sterile syringe with sterile needle is used for injection. Patients should receive 3 doses of 0.5 mL each, with an interval of 4 weeks between vaccinations.

Example 7

Preparation of an Immunogenic Compound

A. Preparation of Immunogenic Compounds

The following immunogenic compound or conjugate was synthesized. It was derived from CRM197 using SMPB as crosslinker molecule (as shown in example 1). The used peptide was a mutated 3S (m3S) peptide consisting of SEQ ID No 6 ($NH_2$—PWNASASNKSLDDIW-COOH) with an additional cysteine residue at its amino-terminus end to allow the chemical coupling the cross linker leading to CRM197-SMPB-Nter(Cys)-m3S For the sake of clarity, the peptide which is termed "Nter(Cys)-m3S" above consists of the 3S peptide of SEQ ID No 7 herein.

The heterobifunctional cross-linker sulfo-SMPB (Sulfo-(Succinimidyl-4-(p-maleimidophenyl) Butyrate) was used. These molecules consist of a maleimide moiety linked by a polyethylene chain to an ester of N-hydroxysuccinimide (Cross-linking of protein by w-maleimido alkanoyl N-hydroxysuccinimido esters. Partis M. D and al. Journal of Protein Chemistry, vol. 2, No 3, 1983). The succinimide moiety can react with amino groups of the protein. Once this reaction has occurred, the maleimide moiety reacts with sulfhydryl groups of the 3S peptides. They are different in length, 7.3 Å for sulfo-MBS and 11.6 Å for sulfo-SMPB. The linker elimination and buffer exchange were made by size exclusion chromatography (SEC).

The coupling reaction was a two-step reaction. The first step was the activation of the CRM197 with the cross-linker. 15 milligrams of linker, diluted in dimethyl sulfoxide were added to 20 milligrams of CRM197 in a volume of 5-20 ml of conjugation buffer (PBS 10 mM pH7-pH7.4) and mixed gently for 30-90 min at room temperature (Protective immunogenicity of two synthetic peptides selected from the amino acid sequence of *Bordetella pertussis* toxin subunit 51. Askelöf P. and al. PNAS, vol. 87, pp 1347-1351, February 1990). This reaction was followed by a purification of the activated CRM197 by SEC (PD 10 column (GE Healthcare, Chalfont St. Giles United Kingdom) or Bio-Gel P2 column (Biorad Marnes-1a-Coquette, France)). Secondly, the activated CRM197 and the 3S-derived peptide were mixed for 30 min-2 hours at room temperature allowing the covalent coupling of the peptide onto the activated CRM197. To block unreacted maleimido groups of activated CRM197, cystein-HCl (SIGMA, Missouri, USA) is added in excess to the solution after the conjugation reaction (A practical approach to crosslinking Mattson G. and al. Molecular Biology Reports 17: 167-183, 1993). This step limited the creation of multimers. The immuno-conjugates were then purified by size exclusion chromatography. The immuno-conjugates were analyzed using an amino acid analysis (AAA) to determine the peptide/CRM197 ratio.

B. Properties of these Immunogenic Compounds

The immuno-conjugate obtained and corresponding to the m3S peptide of SEQ ID No 7 which comprises a Cys residue at the N-terminal end, the CRM197 carrier and SMPB as a linker was found spontaneously soluble in water or in 0.9% NaCl solution. The immunogenicity of such immuno-conjugates was further studied in example 10 below.

Example 8

Immunogenicity of the Immunogenic Compound of Example 9

A. Materials and Methods

A.1. The immuno-conjugate compounds tested in Example 10 have been prepared as disclosed in Example 9.

It was formulated as described in example 3. For that purpose Alhydrogel® 2% (aluminium hydroxide gel) was used as an adjuvant and purchased from Brenntag (Frederikssund, Denmark). Alhydrogel® was used at a final concentration of 1 mg/mL of $Al^{3+}$ ions, which final concentration is adapted to the administration of 50 µg of $Al^{3+}$ ions per injection.

A.2. Animals

Animals were BALB/cByJ females provided by Charles River Laboratories (Lyon, France) which were 8 weeks-old at day 0 of the experiment.

A.3. Method of Administration

The vaccine preparation described in example 5 was injected to mice by the intramuscular route at a dose of 2 µg, as expressed as the amount of antigenic peptide equivalent.

Mice were injected intramuscularly with 50 µl of each composition tested at Day 0, Day 14, Day 28 and Day 169 and Day 212, respectively.

A.5. ELISA Assay

The ELISA assay was designed to perform the measurement of IgG antibodies that would recognized the peptides of SEQ ID No 6, also called anti-m3S peptide antibodies.

The anti-m3S IgG antibody titers were determined by an Enzyme-Linked ImmunoSorbent Assay (ELISA).

Eight dilutions of the day 169, Day 204 and Day 260 serums were tested (1/3000, 1/6000, 1/12000, 1/24000, 1/48000, 1/96000, 1/192000, and 1/384000). The antigen coated to the Nunc Maxisorp micro plates is a m3S peptide conjugated to bovine serum albumin (BSA) with a different linker than the one used for the synthesis of the immunoconjugate s: SMCC (succinimidyl-4-(N-maleimidomethyl) cyclohexane-1-carboxylate) (produced from Imject® Maleimide Activated BSA Protein Kits purchased from Thermo Fisher Scientific, Waltham, USA). The anti-m3S IgG antibodies are revealed by a colorimetric reaction using a goat anti-mouse IgG (Fc), conjugated to the HorseRadish Peroxydase (HRP) (Jackson Immunoresearch, West Grove, USA), and the HRP substrate: the tetramethylbenzidine (TMB) (Sigma, Missouri, USA).

B. Results

IgG titers of anti-3S antibodies were measured by the ELISA assay described in the Materials and Methods section.

Figure 6:
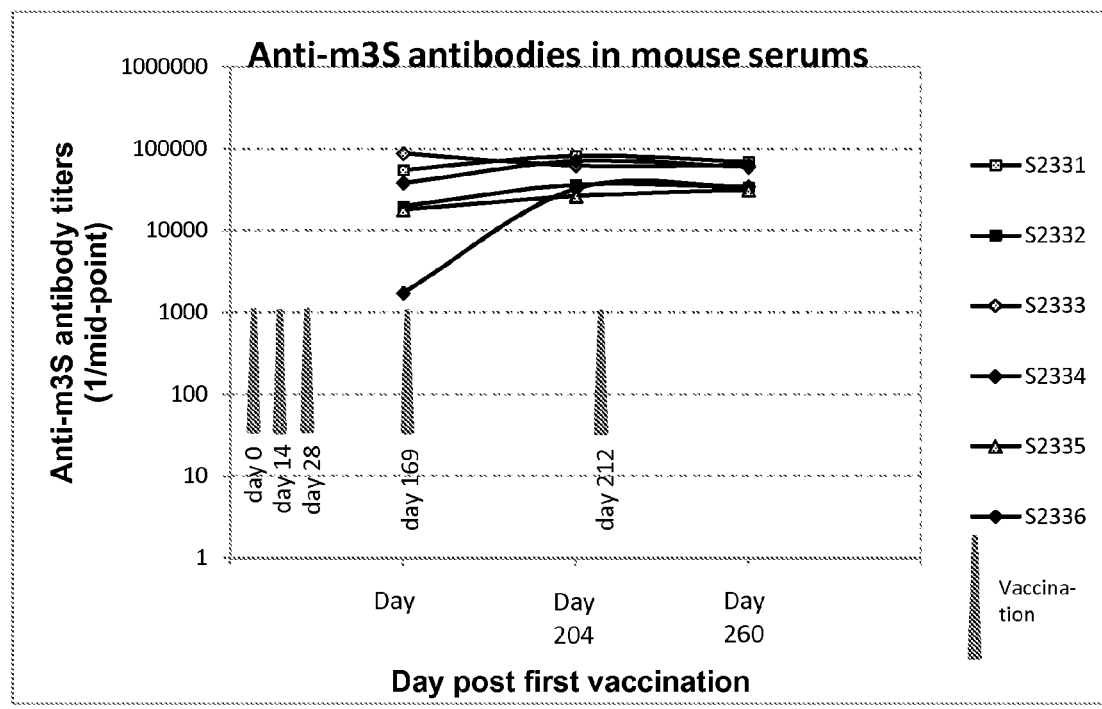
FIG. 6 illustrates the raising of anti-35-peptide antibodies upon immunisation with m3S16Nter peptide conjugated with CRM197. Each symbol represents the results obtained from one mouse and six mice were immunized therewith. Mice were injected at days 0, 14, 28, 169 and 212, respectively, as illustrated by the corresponding arrows. Abscissa: time period following the first injection of the immunoconjugate as expressed in days. Ordinate: anti-3S antibody titers as expressed as 1/midpoint.

The results are depicted in FIG. 6.

The results of FIG. 6 show that the immunoconjugate compound comprising CRM197 as the carrier protein induces high anti-m3S antibody production at Day 169 after 3 vaccinations at day 0, day 14 and day 28.

The results of FIG. 6 show that the immunoconjugate compound comprising CRM197 as the carrier protein induces high anti-m3S antibody production at Day 260 after 4 vaccinations at day 0, day 14 and day 28 and day 169.

TABLE 7

| SEQ ID | Type | Description |
| --- | --- | --- |
| 1 | Peptide | Central portion of peptide of formula (I) |
| 2 | Peptide | Central portion of peptide of formula (IIa) |
| 3 | Peptide | Nt peptide |
| 4 | Peptide | Ct peptide |
| 5 | Peptide | Cys(Nter) 3S |
| 6 | Peptide | Central portion of peptide of formula (IIb) |
| 7 | Peptide | Cys(Nter) m3S |
| 8 | Peptide | CRM197 |

The invention claimed is:

1. An immunogenic compound comprising a peptide of the following formula (I)

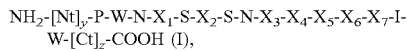

wherein:
- y is an integer meaning 0 or 1,
- z is an integer meaning 0 or 1,
- Nt consists of a peptide having from 1 to 100 amino acids in length,
- Ct consists of a peptide having from 1 to 100 amino acids in length,
- $X_1$ is an amino acid selected from the group consisting of A (Alanine), T (threonine), S (Serine) and N (Asparagine),
- $X_2$ is an amino acid selected from the group consisting of W (Tryptophane) and A (Alanine),
- $X_3$ is an amino acid selected from the group consisting of K (Lysine) and R (Arginine),
- $X_4$ is an amino acid selected from the group consisting of S (Serine) and T (Threonine),
- $X_5$ is an amino acid selected from the group consisting of L (Leucine), Y (Tyrosine) and Q (Glutamine),
- $X_6$ is an amino acid selected from the group consisting of D (Aspartic acid), N (Asparagine), E (Glutamic acid), S (Serine), G (Glycine) and K (Lysine), and
- $X_7$ is an amino acid selected from the group consisting of D (Aspartic acid), Q (Glutamine), L (Leucine), A (Alanine), K (Lysine) and E (Glutamic acid), which peptide of formula (I) is covalently linked to a carrier protein consisting of a CRM197 protein.

2. The immunogenic compound according to claim 1 comprising a peptide selected from the group consisting of the following formulae (VIa) and (VIb):

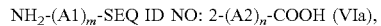

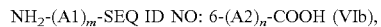

wherein :
- m is an integer meaning 0 or 1,
- n is an integer meaning 0 or 1,
- A1 is an amino acid residue, and
- A2 is an amino acid residue, which peptide of formula (VIa) or (VIb) is covalently linked to a carrier protein consisting of a CRM197 protein.

3. The immunogenic compound according to claim 1, wherein the peptide of formula (I) is selected from the group consisting of SEQ ID NO: 5 and SEQ ID NO: 7.

4. The immunogenic compound according to claim 1, wherein the peptide of formula (I) is covalently bound to the CRM197 protein by its N-terminal end amino acid residue.

5. The immunogenic compound according to claim 1, wherein the peptide of formula (I) is covalently bound to the CRM197 protein through a linker moiety.

6. The immunogenic compound according to claim 5, wherein the linker moiety is the reaction product of a linker agent having two reactive groups with both CRM197 and a peptide of formula (I).

7. The immunogenic compound according to claim 6, wherein the linker moiety consists of succimidyl 4-[p-maleimidophenyl]butyrate (SMPB) and sulfo-SMPB.

8. A composition comprising an immunogenic compound according to claim 1 in combination with one or more immunoadjuvant substances.

9. The composition according to claim 8, which is adapted to form a ready-to-use vaccine composition comprising an amount of the immunogenic compound ranging from 0.01 µg to 200 µg per dosage unit as expressed in antigenic peptide equivalent.

10. The composition according to claim 8, wherein the immunoadjuvant substance consists of aluminium hydroxide $(Al(OH)_3)$.

11. The composition according to claim 8, wherein the immunoadjuvant substance comprises aluminium hydroxide $(Al(OH)_3)$)and wherein the composition is adapted to form a ready-to-use vaccine composition comprising a final concentration of aluminium hydroxide ranging from 0.05 mg/mL to 5 mg/mL, as expressed as $Al^{3+}$ ions content.

12. The composition according to claim 8, which is adapted to form a ready-to-use vaccine composition further comprising a final concentration of 0.1 mM to 50 mM sodium phosphate.

13. The composition according to claim 8, which is in a liquid form or in a solid form, including in a lyophilized form.

14. The composition according to claim 9, which is adapted to form a ready-to-use vaccine composition comprising an amount of the immunogenic compound ranging from 0.05 µg to 50 µg per dosage unit as expressed in antigenic peptide equivalent.

15. The composition according to claim 14, which is adapted to form a ready-to-use vaccine composition comprising an amount of the immunogenic compound ranging from 0.1 µg to 20 µg per dosage unit as expressed in antigenic peptide equivalent.

16. The composition according to claim 11, which is adapted to form a ready-to-use vaccine composition comprising a final concentration of aluminium hydroxide ranging from 0.1 mg/mL to 2 mg/mL as expressed as $Al^{3+}$ ions content.

17. The composition according to claim 16, which is adapted to form a ready-to-use vaccine composition comprising a final concentration of aluminium hydroxide of about 1 mg/mL as expressed as $Al^{3+}$ ions content.

18. The composition according to claim 12, which is adapted to form a ready-to-use vaccine composition comprising a final concentration ranging from 0.5 mM to 15 mM sodium phosphate.

19. The composition according to claim 18, which is adapted to form a ready-to-use vaccine composition comprising a final concentration of about 1 mM sodium phosphate.

20. A composition for administration to a mammal, comprising a compound according to claim 1 and a pharmaceutically acceptable carrier.

* * * * *

```
                             SEQUENCE LISTING

<160> NUMBER OF SEQ ID NOS: 8

<210> SEQ ID NO 1
<211> LENGTH: 15
<212> TYPE: PRT
<213> ORGANISM: artificial sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: X means Alanine, Threonine, Serine or
      Asparagine
<220> FEATURE:
<221> NAME/KEY: MISC_FEATURE
<222> LOCATION: (6)..(6)
<223> OTHER INFORMATION: X means Tryptophane or Alanine
<220> FEATURE:
<221> NAME/KEY: MISC_FEATURE
<222> LOCATION: (9)..(9)
<223> OTHER INFORMATION: X means Lysine or Arginine
<220> FEATURE:
<221> NAME/KEY: MISC_FEATURE
<222> LOCATION: (10)..(10)
<223> OTHER INFORMATION: X means Serine or Threonine
<220> FEATURE:
<221> NAME/KEY: MISC_FEATURE
<222> LOCATION: (11)..(11)
<223> OTHER INFORMATION: X means Leucine, Tyrosine or Glutamine
<220> FEATURE:
<221> NAME/KEY: MISC_FEATURE
<222> LOCATION: (12)..(12)
<223> OTHER INFORMATION: X means Aspartic acid, Asparagine, Glutamic
      acid, Serine, Glycine, or Lysine
<220> FEATURE:
<221> NAME/KEY: MISC_FEATURE
<222> LOCATION: (13)..(13)
<223> OTHER INFORMATION: X means Aspartic acid, Glutamine, Leucine,
      Alanine, Lysine and Glutamic acid

<400> SEQUENCE: 1

Pro Trp Asn Xaa Ser Xaa Ser Asn Xaa Xaa Xaa Xaa Xaa Ile Trp
1               5                   10                  15

<210> SEQ ID NO 2
```

```
<211> LENGTH: 15
<212> TYPE: PRT
<213> ORGANISM: artificial sequence
<220> FEATURE:
<223> OTHER INFORMATION: peptide

<400> SEQUENCE: 2

Pro Trp Asn Ala Ser Trp Ser Asn Lys Ser Leu Asp Asp Ile Trp
1               5                   10                  15

<210> SEQ ID NO 3
<211> LENGTH: 5
<212> TYPE: PRT
<213> ORGANISM: artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: X means Threonine or Proline
<220> FEATURE:
<221> NAME/KEY: MISC_FEATURE
<222> LOCATION: (4)..(4)
<223> OTHER INFORMATION: X means Alanine, Threonine or Asparagine

<400> SEQUENCE: 3

Cys Xaa Thr Xaa Val
1               5

<210> SEQ ID NO 4
<211> LENGTH: 5
<212> TYPE: PRT
<213> ORGANISM: artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X means Aspartic acid, Glutamine, Glutamic
      acid or Asparagine
<220> FEATURE:
<221> NAME/KEY: MISC_FEATURE
<222> LOCATION: (2)..(2)
<223> OTHER INFORMATION: X means Asparagine, Histidine, Serine or Lysine

<400> SEQUENCE: 4

Xaa Xaa Met Thr Trp
1               5

<210> SEQ ID NO 5
<211> LENGTH: 16
<212> TYPE: PRT
<213> ORGANISM: artificial sequence
<220> FEATURE:
<223> OTHER INFORMATION: peptide

<400> SEQUENCE: 5

Cys Pro Trp Asn Ala Ser Trp Ser Asn Lys Ser Leu Asp Asp Ile Trp
1               5                   10                  15

<210> SEQ ID NO 6
<211> LENGTH: 15
<212> TYPE: PRT
<213> ORGANISM: artificial sequence
<220> FEATURE:
<223> OTHER INFORMATION: peptide

<400> SEQUENCE: 6

Pro Trp Asn Ala Ser Ala Ser Asn Lys Ser Leu Asp Asp Ile Trp
1               5                   10                  15
```

<210> SEQ ID NO 7
<211> LENGTH: 16
<212> TYPE: PRT
<213> ORGANISM: artificial sequence
<220> FEATURE:
<223> OTHER INFORMATION: peptide

<400> SEQUENCE: 7

```
Cys Pro Trp Asn Ala Ser Ala Ser Asn Lys Ser Leu Asp Asp Ile Trp
1               5                   10                  15
```

<210> SEQ ID NO 8
<211> LENGTH: 535
<212> TYPE: PRT
<213> ORGANISM: Corynebacterium diphtheriae

<400> SEQUENCE: 8

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300
```

```
Ser Ile Leu Pro Gly Ile Gly Ser Val Met Gly Ile Ala Asp Gly Ala
305             310             315             320

Val His His Asn Thr Glu Glu Ile Val Ala Gln Ser Ile Ala Leu Ser
                325             330             335

Ser Leu Met Val Ala Gln Ala Ile Pro Leu Val Gly Glu Leu Val Asp
            340             345             350

Ile Gly Phe Ala Ala Tyr Asn Phe Val Glu Ser Ile Ile Asn Leu Phe
            355             360             365

Gln Val Val His Asn Ser Tyr Asn Arg Pro Ala Tyr Ser Pro Gly His
    370             375             380

Lys Thr Gln Pro Phe Leu His Asp Gly Tyr Ala Val Ser Trp Asn Thr
385             390             395             400

Val Glu Asp Ser Ile Ile Arg Thr Gly Phe Gln Gly Glu Ser Gly His
                405             410             415

Asp Ile Lys Ile Thr Ala Glu Asn Thr Pro Leu Pro Ile Ala Gly Val
                420             425             430

Leu Leu Pro Thr Ile Pro Gly Lys Leu Asp Val Asn Lys Ser Lys Thr
            435             440             445

His Ile Ser Val Asn Gly Arg Lys Ile Arg Met Arg Cys Arg Ala Ile
            450             455             460

Asp Gly Asp Val Thr Phe Cys Arg Pro Lys Ser Pro Val Tyr Val Gly
465             470             475             480

Asn Gly Val His Ala Asn Leu His Val Ala Phe His Arg Ser Ser Ser
                485             490             495

Glu Lys Ile His Ser Asn Glu Ile Ser Ser Asp Ser Ile Gly Val Leu
            500             505             510

Gly Tyr Gln Lys Thr Val Asp His Thr Lys Val Asn Ser Lys Leu Ser
        515             520             525

Leu Phe Phe Glu Ile Lys Ser
            530             535
```